United States Patent
Chandak et al.

(10) Patent No.: US 11,916,576 B2
(45) Date of Patent: Feb. 27, 2024

(54) SYSTEM AND METHOD FOR EFFECTIVE COMPRESSION, REPRESENTATION AND DECOMPRESSION OF DIVERSE TABULATED DATA

(71) Applicant: KONINKLIJKE PHILIPS N.V., Eindhoven (NL)

(72) Inventors: Shubham Chandak, Menlo Park, CA (US); Yee Him Cheung, Boston, MA (US)

(73) Assignee: Koninklijke Philips N.V., Eindhoven (NL)

(*) Notice: Subject to any disclaimer, the term of this patent is extended or adjusted under 35 U.S.C. 154(b) by 51 days.

(21) Appl. No.: 17/767,070

(22) PCT Filed: Oct. 17, 2020

(86) PCT No.: PCT/EP2020/079298
§ 371 (c)(1),
(2) Date: Apr. 7, 2022

(87) PCT Pub. No.: WO2021/074440
PCT Pub. Date: Apr. 22, 2021

(65) Prior Publication Data
US 2022/0368347 A1 Nov. 17, 2022

Related U.S. Application Data

(60) Provisional application No. 62/956,952, filed on Jan. 3, 2020, provisional application No. 62/923,141, filed on Oct. 18, 2019.

(51) Int. Cl.
*G06F 16/13* (2019.01)
*G06F 21/60* (2013.01)
*H03M 7/30* (2006.01)

(52) U.S. Cl.
CPC ......... *H03M 7/6082* (2013.01); *G06F 16/13* (2019.01); *G06F 21/604* (2013.01); *H03M 7/70* (2013.01)

(58) Field of Classification Search
CPC combination set(s) only.
See application file for complete search history.

(56) References Cited

U.S. PATENT DOCUMENTS

| | | | |
|---|---|---|---|
| 10,778,246 B2* | 9/2020 | Constantinescu | ...... G16B 30/10 |
| 11,393,559 B2* | 7/2022 | Molyneaux | ............ G16B 20/00 |

(Continued)

FOREIGN PATENT DOCUMENTS

WO  2018071055 A1  4/2018

OTHER PUBLICATIONS

"The Variant Call Format Specification", http://samtools.github.io/hts-specs/VCFv4.3.pdf Jul. 21, 2021.
(Continued)

*Primary Examiner* — Jorge A Casanova

(57) ABSTRACT

A method for controlling compression of data includes accessing genomic annotation data in one of a plurality of first file formats, extracting attributes from the genomic annotation data, dividing the genomic annotation data into multiple chunks, and processing the extracted attributes and chunks into correlated information. The method also includes selecting different compressors for the attributes and chunks identified in the correlated information and generating a file in a second file format that includes the correlated information and information indicative of the different compressors for the chunks and attributes indicated in the correlated information. The information indicative of the different compressors is processed into the second file format to allow selective decompression of the attributes and chunks indicated in correlated information.

18 Claims, 23 Drawing Sheets

(56) References Cited

U.S. PATENT DOCUMENTS

| | | | |
|---|---|---|---|
| 2013/0031092 A1 | 1/2013 | Bhola et al. | |
| 2013/0132353 A1* | 5/2013 | Mande | G16B 30/00 707/693 |
| 2014/0232574 A1 | 8/2014 | Aloni et al. | |
| 2017/0177597 A1* | 6/2017 | Asimenos | G06F 16/188 |
| 2018/0052953 A1* | 2/2018 | Ganeshalingam | G16B 30/00 |
| 2018/0089369 A1* | 3/2018 | Semenyuk | G16B 50/00 |
| 2018/0121601 A1 | 5/2018 | Hahm et al. | |

OTHER PUBLICATIONS

Kent, W. James, et al. "BigWig and BigBed: enabling browsing of large distributed datasets." Bioinformatics 26.17 (2010): 2204-2207.

Abdennur, Nezar, and Leonid Mirny. "Cooler: scalable storage for Hi-C data and other genomically-labeled arrays." BioRxiv (2019): 557660.

Zheng, Xiuwen, et al. "SeqArray—a storage-efficient high-performance data format for WGS variant calls." Bioinformatics 33.15 (2017): 2251-2257.

Alberti, Claudio, et al. "An introduction to MPEG-G, the new ISO standard for genomic information representation." pioRxiv(2018): 426353.

Danek, Agnieszka, and Sebastian Deorowicz. "GTC: how to maintain huge genotype collections in a compressed form." Bioinformatics 34.11 (2018): 1834-1840.

CSI index, http://samtools.github.io/hts-specs/CSIv1.pdf downloaded Apr. 5, 2022.

International Search Report and Written Opinion from PCT/EP2020/079298 dated Jan. 20, 2021.

* cited by examiner

Annotation file

| Field | Brief description | Type |
|---|---|---|
| File header | | File_header (§T2) |
| File protection info | Access control policy | Gen_info (§T3) |
| File metadata | Metadata/linkage | Gen_info (§T3) |
| File traceability info | Commands used to generate data | Gen_info (§T3) |
| nTables | Number of tables stored in file (e.g., multiple resolutions) | |
| For i in 1 ...nTables: | | |
| Table ID [i] | Unique table identifier | Integer |
| TableInfo [i] | Table information (e.g., resolution) | Gen_info (§T3) |
| ByteOffset [i] | Byte offset of table i in file | Integer |
| nCompressors | Number of distinct compressors used in the different attributes stored later | Integer |
| For i in nCompressors: | | |
| Compressor [i] | | Comp_info (§T4) |
| For i in 1 ...nTables [i] | | |
| Table [i] | | Table (§T5) |

310 — File header
320 — File protection info
330 — File metadata
340 — File traceability info
351 — nTables / For i in 1 ...nTables:
352 — Table ID [i]
353 — TableInfo [i]
354 — ByteOffset [i]
361 — nCompressors / For i in nCompressors:
362 — Compressor [i]

FIG. 4

File header 310

| Field | Brief description | Type |
|---|---|---|
| File name | | String |
| File type | e.g. "Variant", "Gene expression", etc. | String |
| File version | For keeping track of updates | String |

FIG. 5

General information structure 320

| Field | Brief description | Type |
|---|---|---|
| Payload size | To allow skipping over this | Integer |
| Payload | Compressed with predefined compressor (e.g., 7z) | Bytes |

FIG. 6

Compressor information structure 360

| Field | Brief description | Type |
|---|---|---|
| CompressorID | Unique compressor identifier | String |
| nDependencies | To allows compression of an attribute based on values of other attributes | Integer |
| CompressorNameList | List of compressor names (or "embedded") | List (string) |
| CompressorParametersList | Parameters required for decompression | List (gen_info) |

363 — CompressorID
364 — nDependencies
365 — CompressorNameList
366 — CompressorParametersList

FIG. 7

| Field | | Brief description | Type |
|---|---|---|---|
| TableID | 1105 | Same as in §T1 | Gen_info (§T3) |
| TableInfo | 1110 | Same as in §T1 | Gen_info (§T3) |
| Table protection | 1020 | Access control policy | Gen_info (§T3) |
| Table metadata | 1030 | Metadata/linkage | Gen_info (§T3) |
| Summary statistics | 1040 | e.g., Count, average value  1140 | List (key-value) |
| nDimensions | 1150 | Number of dimensions | Integer |
| For i in 1 ... nDimensions: | | | |
|    Size [i] | | Size of dimension i | Integer |
|    Dimension name [i] | | | |
|    Dimension metadata [i] | | Metadata/linkage | Gen_info (§T3) |
| If nDimensions == 2: | | | |
|    Symmetry flag | | True if 2d array is symmetric | Bool |
| | | | |
| n AttributesMain | 1160 | | |
| For i in 1 ... nAttributesMain: | | | |
|    Attribute info main [i] | | | Attr_info (§T6) |
| Byte offset main | | Byte offset of index main | Integer |
| If n dimensions > 1: | | Dimension-specific attributes | |
|    For i in 1 ... nDimensions: | | | |
|    nAttributes dim [i] | | Number of dimension specific attributes | Integer |
| For j in 1 ... nAttributes dim [i] | | | |
|    Attribute info dim [i][j] | | | Attr_info (§T6) |
|    Byte offset dim [i] | | Byte offset of index dim [i] | Integer |
| | | | |
| Index main | | | Index (§T7) |
| Data payloads main | | | Data (§T9) |

FIG. 11

Attribute information structure

| Field | | Brief description | Type |
|---|---|---|---|
| AttributeInfoSize | 1205 | To allow skipping over structure | Integer |
| Attribute ID | 1210 | Unique attribute identifier | Integer |
| AttributeName | 1215 | | String |
| AttributeMetadata | 1220 | Metadata/linkage/grouping of attributes | Gen_info (§T3) |
| Attribute type | 1225 | Fundamental types (e.g., int, char, float, string) or derived types (e.g., fixed- length, variable-length array) | String |
| DefaultValue | 1230 | For sparse encoding if most values match default | Attribute type |
| Summary statistics | 1235 | e.g., Count, average value | List (key-value) |
| CompressorID | 1240 | Compressor used for this attribute | Integer |
| For i in 1 ... nDependencies: | | nDependencies defined in §T4 | |
|   If nDimensions > 1: | | | |
|     Dimension | | If this is an attribute of the main n-dimensional table, this tells which dimension contains the dependency attribute (set to nDimensions+1 if dependency attribute is also in main nDimensional table) | Integer |
|     AttributeID | | AttributeID containing the dependency | Integer |
| CompressorCommonData size | | | Integer |
| CompressorCommonData | | To store codebooks/statistical models for the compressor that are common to all chunks | Bytes |

FIG. 12

Index structure

| Field | Brief description | Type |
|---|---|---|
| AttributeDependentChunks 1510 | Flag denoting whether chunks sizes are dependent on the attributes or if same chunking is used for all attributes | Bool |
| If not AttributeDependentChunks: | | |
|    ChunksStructure 1515 | | |
| Else: | | Chunks (§T8) |
|    For i in 1 ... nAttributes: | | |
|      Chunks structure [i] 1520 | | |
| // Additional attribute specific indexes 1525 | | |
| n Additional indexes | Number of additional indexes for faster query based on certain attributes (e.g., chromosome and position) - these return the chunk number(s) containing the desired query results | Integer |
| For i in 1 ... nAdditionalIndexes: | | |
|    AttributeIDsIndexed [i] 1530 | List of attributes indexed | List (integer) |
|    IndexType [i] 1535 | Index type (e.g., CSI index for chromosome and genomic position or B-tree for database type queries) | String |
|    IndexSize [i] 1540 | To allow skipping over index | Integer |
|    IndexData [i] 1545 | Actual index data, specifics depend on IndexType [i] | Bytes |

FIG. 15

Chunks structure

| Field | | Brief description | Type |
|---|---|---|---|
| nChunks | 1605 | Number of chunks | Integer |
| VariableSizeChunks | 1610 | Flag denoting whether chunks sizes are variable or fixed (except at the boundary of each dimension) | Bool |
| If VariableSizeChunks: | | | |
|   For j in 1 ... nChunks: | | | |
| For k in 1 ... nDimensions: | | | |
|   StartIndex [j][k] | 1615 | Start position of chunk along dimension k | Integer |
|   EndIndex [j][k] | 1620 | End position of chunk along dimension k | Integer |
|   ByteOffset [j] | 1625 | Byte offset of chunk j in file | Integer |
| Else: | | | |
|   For k in 1 ... nDimensions: | | | |
|     ChunkSize [k] | | For fixed size chunks, sufficient to store size of chunk in each dimension | Integer |
|   For j in 1 ... nChunks: | | | |
|     ByteOffset [j] | | Byte offset of chunk i in file | Integer |

FIG. 16

Data payload

| Field | Brief description | Type |
|---|---|---|
| If not AttributeDependentChunks: | | |
|   For i in 1... nChunks: | | |
|     For j in 1... nAttributes: | | |
|       Payload size [i][j] | To allow skipping over certain attributes | Integer |
|       Payload [i][j] | Compressed payload | Bytes |
| Else: | | |
|   For j in 1... nAttributes: | | |
|     For i in 1... nChunks: | | |
|       Payload size [i][j] | | Integer |
|       Payload [i][j] | Compressed payload | Bytes |

FIG. 21

SYSTEM AND METHOD FOR EFFECTIVE COMPRESSION, REPRESENTATION AND DECOMPRESSION OF DIVERSE TABULATED DATA

CROSS-REFERENCE TO RELATED APPLICATIONS

This application is related to U.S. Provisional Patent Application Ser. No. 62/923,141, filed on Oct. 18, 2019, the entire contents of which are hereby incorporated herein by reference for all purposes.

This application is related to U.S. Provisional Patent Application Ser. No. 62/923,113, filed on Oct. 18, 2019, the entire contents of which are hereby incorporated herein by reference for all purposes.

This application is related to U.S. Provisional Patent Application Ser. No. 62/956,941, entitled "Customizable Delimited Text Compression Framework," filed concurrently with the present application, the entire contents of which are hereby incorporated by reference herein for all purposes.

TECHNICAL FIELD

One or more embodiments herein relate to managing compression and decompression of information, including but not limited to tabulated data and delimited text files.

BACKGROUND

Genomic data has proven to be important for many research applications. When in raw form, genomic data may include a large number of sequenced genomes. In some cases, the number of sequences is unmanageably large. Therefore, various attempts have been made to extract, or better interpret, relevant information from the raw data.

One processing technique involves use of an annotation tool. Such a tool may be used to define coding regions m the genome data and their corresponding locations. Annotation may also provide an indication of the number and spatial distribution of repeat regions, which may, convey information regarding disease and genetic anomalies. Some examples of genomic annotation data include mapping statistics, quantitative browser tracks, variants, genome functional annotations, gene expression data, and Hi-C contact matrices.

Annotation data (and other genome-related information) are currently represented in various file formats, e.g., variant call format (VCF), browser extensible data (BED) format, and wiggle (WIG) format. These formats are incompatible with one another. Consequently, their use raises issues relating to interoperability and the need to perform frequent conversions between formats in order to allow the data to be visualized. Also, the lack of a single unified, standardized format has stifled the work on compression algorithms and has led to widespread use of suboptimal compression algorithms (e.g., gzip).

Drawbacks associated with existing algorithms for compressing genomic information relate to a lack of selectivity, among other things. For example, genomic annotation data typically includes multiple fields (attributes) with different statistical characteristics. Existing algorithms compress all of the fields together, which eliminates the ability to selectively recognize, use, and extract information in the individual data fields. Also, existing algorithms do not allow for extraction of specific fields without decompressing all the attributes.

Other drawbacks relate to the inability of existing compression methods to be generically applicable. For example, these methods rely on only one or a small set of standard compressors, which makes them applicable to only one type of annotation data. These methods are also unable to perform selective encryption, nor do they have the ability to link multiple annotation datasets with each other and with sequencing data. Some specialized methods have been proposed. However, many of these methods are based on disk-based array management tools (e.g., TileDB and HDF5), which lack high-level features, for example, including but not limited to metadata, linkages, and attribute-specific indexing.

SUMMARY

A brief summary of various example embodiments is presented below. Some simplifications and omissions may be made in the following summary, which is intended to highlight and introduce some aspects of the various example embodiments, but not to limit the scope of the invention. Detailed descriptions of example embodiments adequate to allow those of ordinary skill in the art to make and use the embodiments follow in later sections.

In accordance with one or more embodiments, a method for controlling compression of data includes accessing genomic annotation data in one of a plurality of first file formats, extracting attributes from the genomic annotation data, dividing the genomic annotation data into chunks, processing the extracted attributes and chunks into correlated information, selecting different compressors for the attributes and chunks identified in the correlated information, and generating a file in a second file format that includes the correlated information and information indicative of the different compressors for the chunks and attributes indicated in the correlated information, wherein the first file formats are incompatible with one another and different from the second file format and wherein the information indicative of the different compressors is processed into the second file format to allow selective decompression of the attributes and chunks indicated in correlated information.

The correlated information may include at least one a table including: first information indicative of one or more of the attributes, and second information corresponding to chunks associated with the one or more attributes indicated in the first information. The first information may include a two-dimensional array of cells, and each cell may identify one or more corresponding attributes included in the chunks corresponding to the two-dimensional array of cells. The first information may include at least one one-dimensional table of dimension-specific attributes relating to the chunks. The genomic annotation data may be divided into chunks of equal size. The genomic annotation data may be divided into chunks of different sizes.

The method may include generating one or more first indexes linking the correlated information, and generating one or more second indexes linking the correlated information to the information indicative of the different compressors, wherein the one or more first indexes and the one or more second indexes are processed into the file of the second file format. The method may include integrating the file in the second file format into an MPEG-G file.

The method may include generating access control policy information for the correlated information, and integrating the access control policy information into the file of the second file format, wherein the access control policy information includes first information indicating a first level of access for a first portion of the correlated information and second information indicating a second level of access for a second portion of the correlated information, and wherein the second level of access is different from a first level of access. The extracted attributes may include at least one of a chromosome attribute and a genome position attribute.

In accordance with one or more embodiments, an apparatus for controlling compression of data includes a memory configured to store instructions and at least one processor configured to execute the instructions to perform operations including: accessing genomic annotation data in one of a plurality of first file formats, extracting attributes from the genomic annotation data, dividing the genomic annotation data into chunks, processing the extracted attributes and chunks into correlated information, selecting different compressors for the attributes and chunks identified in the correlated information, and generating a file in a second file format that includes the correlated information and information indicative of the different compressors for the chunks and attributes indicated in the correlated information. The first file formats are incompatible with one another and different from the second file format. The information is indicative of the different compressors is processed into the second file format to allow selective decompression of the attributes and chunks indicated in the correlated information.

The correlated information may include at least one table including: first information indicative of one or more of the attributes, and second information corresponding to chunks associated with the one or more attributes indicated in the first information. The first information may include a two-dimensional array of cells and wherein each cell identifies one or more corresponding attributes included in the chunks corresponding to the two-dimensional array of cells. The first information may include at least one one-dimensional table of dimension-specific attributes relating to the chunks. The genomic annotation data may be divided into chunks of equal size. The genomic annotation data may be divided into chunks of different sizes.

The at least one processor may be configured to execute the instructions to: generate one or more first indexes linking the correlated information, and generate one or more second indexes linking the correlated information to the information indicative of the different compressors, wherein the one or more first indexes and the one or more second indexes are processed into the file of the second file format. The at least one processor is configured to execute the instructions to integrate the file in the second file format into an MPEG-G file.

The at least one processor may be configured to execute the instructions to: generate access control policy information for the correlated information, and integrate the access control policy information into the file of the second file format, wherein the access control policy information includes first information indicating a first level of access for a first portion of the correlated information and second information indicating a second level of access for a second portion of the correlated information, and wherein the second level of access is different from a first level of access.

The extracted attributes may include at least one of a chromosome attribute and a genome position attribute.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate example embodiments of concepts found in the claims and explain various principles and advantages of those embodiments.

These and other more detailed and specific features are more fully disclosed in the following specification, reference being had to the accompanying drawings, in which:

FIG. 4 illustrates an embodiment for processing information into an annotation file for the genomic annotation data;

FIG. 5 illustrates an embodiment for processing information into a file header of the unified, standardized file;

FIG. 6 illustrates an embodiment for processing information for the unified, standardized file;

FIG. 7 illustrates an embodiment for processing compression information for the unified, standardized file;

FIG. 11 illustrates an embodiment for processing additional attribute-related information;

FIG. 12 illustrates an embodiment for processing attribute information;

FIG. 15 illustrates an embodiment for processing index information;

FIG. 16 illustrates an embodiment for processing chunks;

FIG. 21 illustrates an embodiment for processing data payloads;

DETAILED DESCRIPTION

Figure 1:
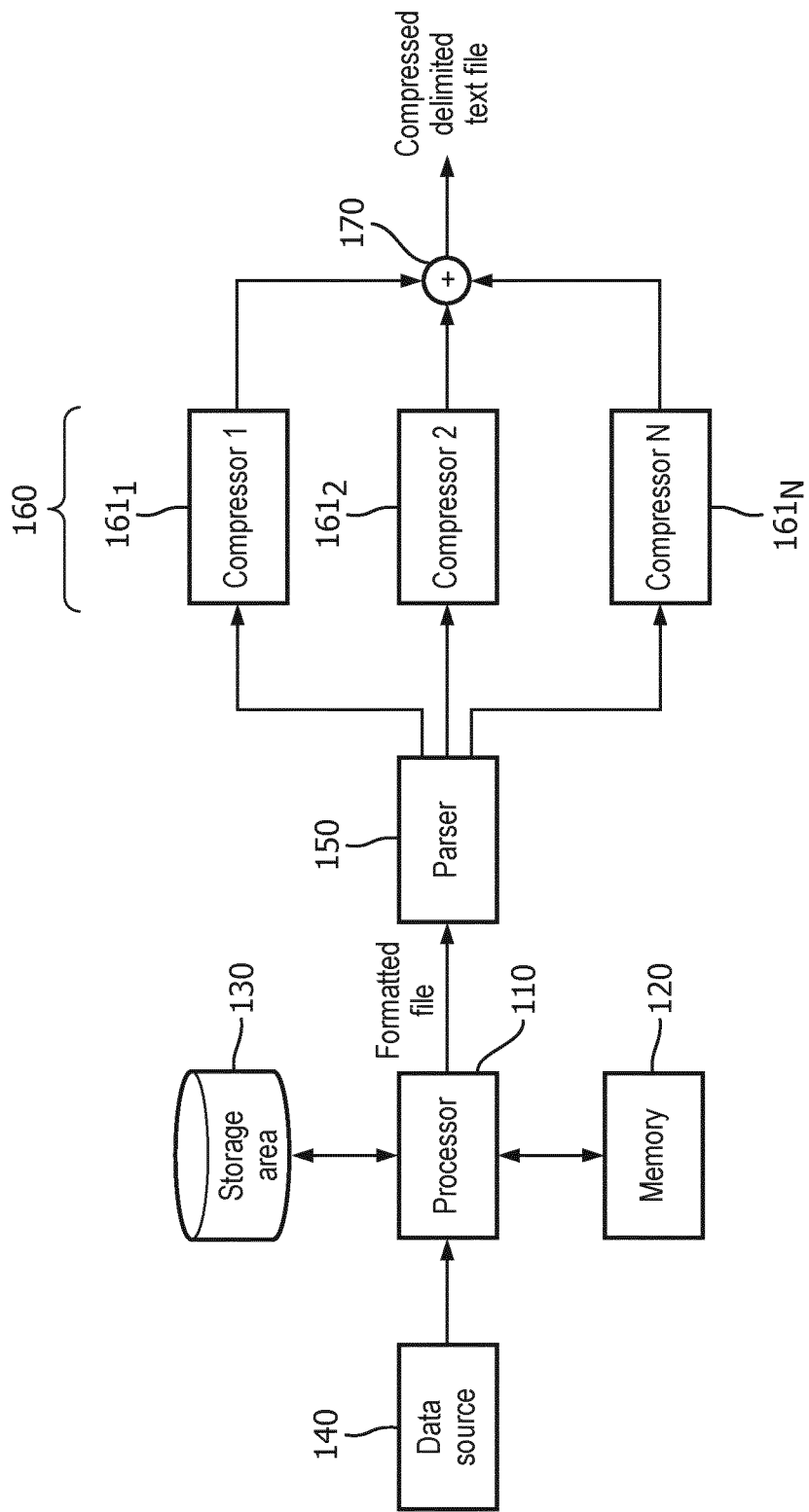
FIG. 1 illustrates an embodiment of a system for controlling compression and decompression for genomic annotation data.

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various example embodiments are not necessarily mutually exclusive, as some example embodiments can be combined with one or more other example embodiments to form new example embodiments. Descriptors such as "first," "second," "third," etc., are not meant to limit the order of elements discussed, are used to distinguish one element from the next, and are generally interchangeable. Values such as maximum or minimum may be predetermined and set to different values based on the application.

Example embodiments describe a system and method for managing the compression of information, including but not limited to tabulated data and delimited text files. The information to be compressed may include genomic information (e.g., annotation, sequencing, or other forms of genome-related data). In other embodiments, another type of information unrelated to genomic information may be managed for compression.

In a genomic application, the system and method may manage the standardization of compression and decompression of the genome data. This includes processing the data to conform to format that reduces or eliminates issues of interoperability and the need to perform frequent conversions between formats in order to allow the data to be visualized. For at least some applications, these features may lead to improvements and optimization of compression algorithms for particular types of data.

In accordance with one or more embodiments, the system and method may process the data to allow for selective compression of different fields, attributes, and/or sections of the data. For example, in some implementations, all of the fields, attributes, or sections of the data (e.g., including ones having different statistical characteristics) may not all be compressed together using the same compression algorithm. Rather, the system and method may be implemented to selectively compress one or more sections of the data and not others, or may be implemented to selectively compress different sections using different compression techniques. The compression techniques selected may be, for example, beneficial or optimal for the different types of data in respective ones of those sections.

This approach of selective compression may, in turn, allow for selective decompression. For example, by selectively compressing the data, the entire data file does not have to be decompressed. Rather, in at least one implementation, one or more sections of the data of interest may be selectively decompressed without decompressing other sections of the compressed data that are not of interest. This may improve efficiency and the ability to avoid encumbrances or other delays during research.

The processing performed by the system and method may also allow at least one embodiment to be generally applicable to all types of data using, for example, large numbers of standard or customized compression algorithms that are to be selectively applied to different data sections. The system and method may also perform selective encryption of the (e.g., differently) compressed sections of the data. The system and method may also be implemented to link multiple annotation datasets with each other and with sequencing data. The system and method may also process the data to include metadata, linkages, and/or attribute-specific indexing.

FIG. 1 illustrates an embodiment of a system for managing the compression of information. The system may be at least partially implemented, for example, at a workstation of a laboratory, research facility, data center, university or corporate setting, or another location where data is processed in connection with an intended application. In another embodiment, the system may be implemented on one or a plurality of connected or networked computers and/or other devices that communicate with one another for purposes of performing the processing operations described herein.

Referring to FIG. 1, the system includes a processor 110, a memory 120, and a storage area 130. The processor 110 executes instructions stored in the memory 120 for purposes of performing operations that involve managing the compression of information. The memory 120 may be any form of non-transitory computer-readable medium that stores the instructions for controlling the processor to perform the operations described herein. The information may be received from a data source 140. The data source may differ depending on, for example, the type of information to be processed. For example, in one implementation the data source 140 may be a software-based tool for generating genomic annotation data. In another implementation, the data source may supply another type of genome-related data or even data that is not related to genome data.

The processor 110 may be locally connected to the data source or connected to the data source over a network. This latter case allows the information processed by the system to be obtained anywhere in the world, provided a network connection can be established between the processor and the data source. The network connection may be a local connection, an internet connection, a virtual private network connection, a connection to a cloud-computing or cloud-based storage device, and/or another type of connection.

The storage area 130 may store the processed results of the processor 110. As described in greater detail below, the processed results may include tabular data or a delimited text file that conforms to a unified, standardized file format that includes multiple fields, attributes, sections, or other portions that may be selectively compressed and/or otherwise processed. The storage area may be or be included in a database, archive, storage-area network, cloud-based storage system, memory located in or coupled to a computer, system or device of the processor, or another type of storage area.

The system of FIG. 1 may include, or be coupled to, one or more additional features for compressing the information that has been processed into the unified, standardized file format. These features may include a parser 150, a compression manager 160, and an aggregator 170.

The parser 150 may parse files that have been stored and subsequently retrieved from the storage area 130. For example, the processor 110 may receive a request for data based on a user input or from another device. The processor may, for example, determine the one or more files stored in the storage area 130 that corresponds to the requested data and, then, retrieve the file(s). The processor 110 may determine which files correspond to the requested data, for example, using an index that links content of the files to one or more identifiers specified in the request. Once the file(s) is/are located, they are retrieved from the storage area 130 and then sent to the parser.

The parser may parse the file in various ways. For example, the file may include delimiters that separate different sections, portions, attributes, fields, etc., that contain different portions of the data (or other type of content) in the file. Using these delimiters as a guide, the parser 150 may parse the file into individual sections (or chunks) that correspond to the request. In one embodiment, the parser may perform these operations in accordance with a predetermined compression schema, which indicates how the file is parsed for purposes of compression.

The compression manager 160 receives the file in the unified, standard format once this file has been retrieved from the storage area 130. The compression manager may include a plurality of compressors $161_1$, $161_2$, ..., $161_N$, where N≥2. Each of the compressors may execute a different compression algorithm to compress different sections of the parsed file. The compression algorithm applied by each compressor may be predetermined given the parsed data or content of the file. For example, one compression algorithm may be more suitable, for terms of efficiency or for other reasons, for compressing certain types of information. Other compression algorithms may be more suitable for compressing other types of information. The compression schema may control which compression algorithm is to be used to compress particular data or content in the file. (The parser may also route the different parsed sections of the file to particular compressors based on instructions derived from the compression schema.) In this way, the compression manager 160 may, therefore, selectively compress the different parsed portions of the file.

The aggregator 170 aggregates, or combines, the different compressed sections into a compressed file according to the unified, standardized file format for compressed files or according to a different format. Once compressed, the selectively compressed file (e.g., a compressed tabular data file or a compressed delimited text file) may be stored in storage area 130, stored in a different storage area, sent to a predetermined location or device, or routed in accordance with another scheme, for example, as determined by predetermined control instructions for the system.

Unified/Standardized Data Processing

In accordance with one or more embodiments, the processor 110 processes the information from the data source to conform to a unified and/or standardized file format, that allows different portions of the file to be selectively compressed (and thus subsequently selectively decompressed). The processing may be performed to allow the genomic annotation data to be stored in a file format that allows one or more predetermined functionalities to be supported. Examples of these functionalities include a fast query, random access, multiple resolutions (e.g., zooms), selective encryption, authentication, access control, and traceability.

In one embodiment, the genomic application data is processed into a format that allows for significant compression gains. This may be achieved, for example, by separating different attributes of the data into sections (e.g., tables). The compressors may then be used to compress respective ones of the separated attributes in the genomic annotation data. In one embodiment, all or a portion of the compressors may be specialized or customized compressors designed to compress the specific attributes of the file to which they are allocated. The processing performed by processor 110 may also generate metadata and linkages for sequencing data associated with the annotations, as well as linkages to other annotation data that may be related or unrelated to the sequencing data. The metadata and/or linkages may be stored in the same unified, standardized format as the genomic application data, thereby allowing seamless integration with an existing file format (e.g., MPEG-G) for sequencing data.

Figure 2:
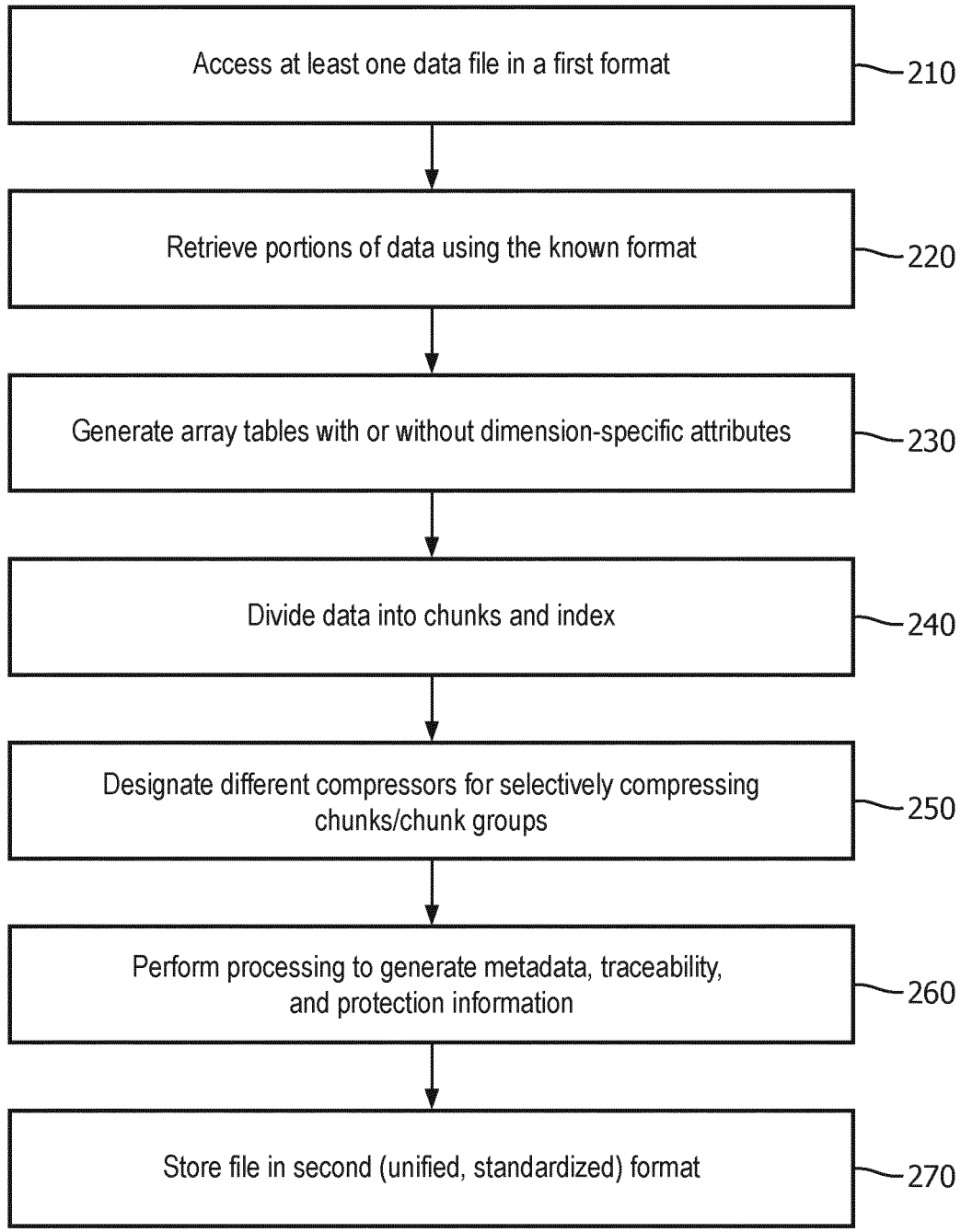
FIG. 2 illustrates a method for controlling compression and decompression for genomic annotation data.

FIG. 2 illustrates a method for managing the compression of information in accordance with a unified, standardized file format. The method may be performed, for example, by the system of FIG. 1 or another system, in accordance with instructions stored in memory for controlling one or more processors to perform the operations described below. For purposes of illustration, it will be assumed that the method is partially or entirely performed by the system of FIG. 1 and that the data is genomic annotation data.

Referring to FIG. 2, the method includes, at 210, receiving data (e.g., genomic annotation data) from the data source 140. The genomic annotation data may be received in an existing format generated, for example, by an annotation tool used to generate the data. One example of the existing format is an MPEG-G format, but the annotation data may be received in a different existing format in another embodiment. The data may be received by processor 110, through a local or network connection, from the data source.

At 220, portions of the genomic annotation data are retrieved for processing into the unified, standardized file format. Because the genomic annotation data is organized according to an existing known format, the content retrieved at each portion of the known format has a specific type of data known to the processor 110. The instructions controlling the processor 110 may therefore retrieve the specific types of data at each portion of the known format in order to generate a new file in the unified, standardized format in accordance with one or more embodiments.

Figure 3:
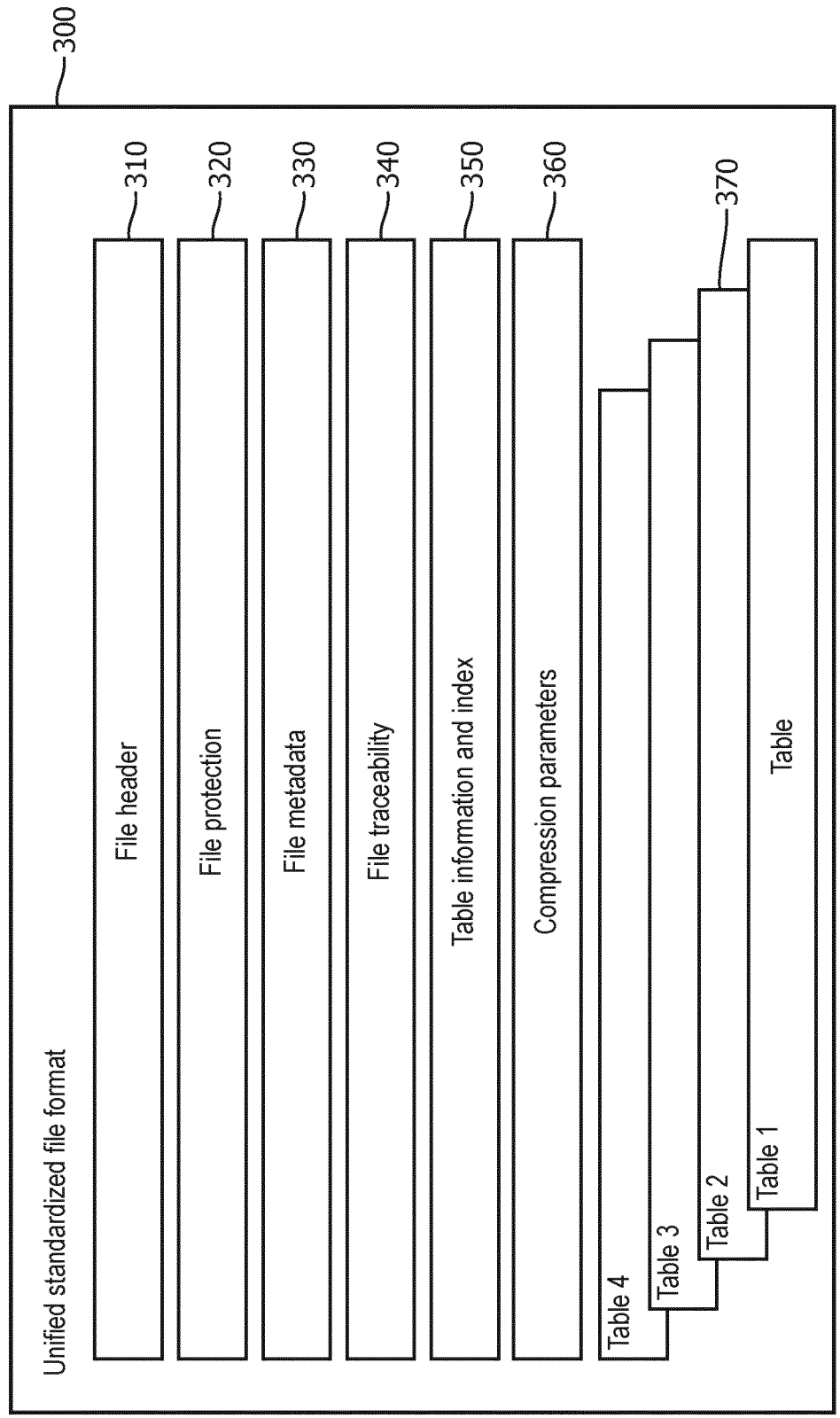
FIG. 3 illustrates an embodiment of a unified, standardized file format for the genomic annotation data.

At 230, the processor 110 executes instructions in memory 120 to process the genomic annotation data so that it conforms to the unified, standard file format 300, for example, as illustrated in FIG. 3. For example, the processor may process the data to generate in a file header section 310, a file protection section 320, a file metadata section 330, a file traceability section 340, a table information and index section 350, a section indicating one or more compression parameters 360, and one or more tables 370. These sections along with a corresponding description is set forth in the chart of FIG. 4, along with other information that is discussed in greater detail below.

The file header section 310 includes various types of identification information. For example, the file header section may include a file name field 311, a file type field 312, and a file version field 313 (e.g., see FIG. 5). The file name field may include a string labeling the file with a name generated, for example, by an annotation tool or based on information from a user. The file type field may include a string indicating a type of the file, e.g., variant, gene expression, etc. The file version field may include a string identifying the purpose and/or version of the file, e.g., this file is for keeping track of updates.

The file protection section 320 may include information relating to an access control policy for the file, which, for example, may be determined by a user, administrator, data owner, or other entity in control of access to and/or dissemination of the data. The access control policy may indicate a same level of access for the entire file or different levels of access to different portions of the file. In one embodiment, the file protection section may include a payload size field 321 and a payload field 322 (e.g., see FIG. 6). The payload size field may include one or more integer values indicating, for example, the size of the protection information payload that enables this field or its associated information to be skipped or to be taken into consideration. The payload field includes information regarding the protection and access control policy for the file.

The file metadata section 330 and the file traceability section 340 may include information as described in greater detail below. In one embodiment, the file protection information, metadata, versioning, and traceability information may be compressed using, for example, a generic compression algorithm, e.g., 7zip. In some implementations, JSON/XML/XACML-based schemas may be used for compressing this information, along with URI (uniform resource identifier) notation (e.g., as performed in MPEG-G part 3).

The table information and index section 350 may include an nTables field 351 indicating the number of tables (n) in the file. In one embodiment, the unified standardized format may store annotation data in multiple tables, e.g., n ≥ 2. In this case, different ones of the multiple tables may store various types of the annotated data. In one case, different tables in the file may be used to store the same genomic annotation data at different resolutions. This case is provided as just one example of the content of the tables. In other embodiments, the tables may store other types of annotation data.

In addition to the nTables field 351, that table information and index section may store a Table ID[i] section 352, a TableInfo[i] section 353, and a ByteOffset[i] section 354. The Table ID[i] section 352 may store one or more integer values indicating unique identifiers for corresponding tables i of the n tables in the file. The TableInfo[i] section 353 may store information indicative of the resolutions of corresponding ones of the tables i of the n tables. The ByteOffset [i] section 354 stores one or more integer values indicating byte offsets for respective ones of the tables i of the n tables in the file. Through this format, basic information about one or more of the tables in the file (e.g., resolution level) may be extracted without needing to read the whole file, for example, using the TableInfo field in a JSON/XML-like format. Similarly, the byte offset of the tables in the compressed file may be available to directly jump to a specific table.

At 240, the genomic data in the received (source) file is divided into a plurality of chunks or chunk groups. The chunks may have a same fixed size or may have variable sizes depending, for example, whether the chunks are attribute-dependent and/or based on other parameters relating to the data. The chunks may be generated, for example, by the parser 150 as previously described.

At 250, different compressors (or compression algorithms) are designated for compressing the divided chunks or chunk groups. The compressors may be outside the unified, standardized file and/or may be internally initiated, for example, by embedded code or a selectable stored in a compression parameter table.

Accordingly, the compression parameters section 360 may include a field 361 indicating the number of different compressors (or compression algorithms) that are used to compress different information (e.g., attributes) included in the tables of the file. This information may be expressed, for example, as one or more integer values. Section 360 may also include a field 362 including information listing the different compressors indexed by unique identifiers. These can be referred to in the tables, thus avoiding repeated description of compressors used in multiple tables or for multiple attributes.

In one embodiment, field 362 (or fields separate from or hierarchically related to field 362 in the compression parameters section 360) may include a CompressorID field 363, an nDependencies field 364, a CompressorNameList field 365, and a CompressorParametersList field 366, as illustrated in FIG. 7.

The CompressorID field 363 may include information (e.g., string) indicating a unique identifier of a corresponding one of the compressors. The CompressorID field may therefore be used to identify the compressors to be used in compressing respective attributes or other portions of the file. In one embodiment, the unique identifier may be used in the tables to point to a corresponding compressor.

The nDependencies field 364 may include information (e.g., one or more integer values) indicating that the compression of an attribute is performed based upon other attributes. For example, the system processor may process information for compression of one attribute using one or more other attributes as side information (provided there is no cyclic dependency). This information may then be included in the nDependencies field 364 of the unified, standardized file format. In one embodiment, an indication of variable nDependencies may denote the number of dependency attributes to be used for decompression (e.g., examples of corresponding attributeIDs are set forth in the attribute information structure in FIG. 12). Compressors such as context-based arithmetic coding may easily support the incorporation of side information. Another mechanism to incorporate the side information from other attributes is to reorder or split the values of the current attribute based on the values of the other attributes, which can bring together similar values and provide better compression. The parameters describe the dependencies used by each compressor in the list.

The CompressorNameList field 365 may include information (e.g., string) indicating a list of compressor names. The compressor names may refer to one or more compressors that are external to the file (e.g., as implemented by a compression module or system processor 110), one or more compressors that are embedded in the file (e.g., through embedded code or an executable), or both. One or more of the compressor names and parameters may correspond to a standard compressor or may describe a decompression mechanism. In one embodiment, one or more of the compressor executables and parameters may be indicated within the CompressorParameters, e.g., by setting CompressorName to "EMBEDDED." In some embodiments, multiple compressors may be used to compress the same attributes or file portions. In this case, multiple compressors may be applied in sequence and indicated in a list included in the unified, standardized file format.

The CompressorParametersList field 366 may include information (e.g., in the form of a list or otherwise) indicating one or more parameters to be used to perform decompression of the information compressed by all or a portion of the named compressors.

At 260, the method includes processing the received (source) file and/or policy information generated by an owner of the data or administrator to generate additional information including metadata, traceability information, linkage information, index(es), and protection information for storage in corresponding fields as described herein.

At 270, the unified, standardized genomic annotation data file is stored for later retrieval. Because the different data chunks have been selectively compressed, only designated portions of the compressed file may be decompressed to access certain information in the file without having to decompress other information in the file. This increases processing speed and user convenience by targeting only that portion of the genomic data that may be of particular interest at any given time.

All or a portion of the information designated in the unified, standardized file may correspond to correlated information that is set forth in tables, structure, indexes, or other types of correlated information that allow for the selective compression and decompression and access of the genomic annotation data. Examples of tables in the correlated information are discussed in greater detail below.

Tables

The tables 370 in each unified standardized file may be related or independent from one another in terms of the attributes and/or other information stored therein. Each table may include a plurality of cells, and each cell may include one or more attributes. Each attribute may have a specific datatype and may be compressed using one of the compressors. When the cells in a table include multiple attributes, the data corresponding to the multiple attributes in each cell of the table may be compressed separately for improved compression and selective access to the attributes when subsequently decompressed. In a genome functional annotation file, the attributes may include, for example, chromosome, start position, end position, feature ID, and feature name.

The compression may be performed differently in different embodiments, e.g., on an attribute-by-attribute basis, cell-by-cell basis, table-by-table basis, etc. For example, groups of cells in a same table may be compressed separately from other groups of cells for these purposes. The cells that have been grouped together may have attributes corresponding to the same data and the other groups of cells may have different attributes corresponding to the same or different data. In one implementation, the attributes in each cell may be compressed using different compression algorithms, or the attributes in one or more cells may be compressed by a first compression algorithm, the attributes in one or more other cells may be compressed using a second compression algorithm, the attributes in one or more other cells may be compressed using a third compression algorithm, and so on.

In an additional implementation, all or a portion of the compressors 161$_1$, 161$_2$, . . . , 161N may execute different compression algorithms that are specialized for different data/attribute types in respective ones of the cells. While examples of a unified, standardized file format are discussed below as including multiple tables, in one embodiment the file format may include only one table.

While in some examples, the content in each cell is described as attributes, the content may include other types of data in other embodiments (e.g., type of data, attributes, characteristics, etc.) or a combination of types of data. For example, the tables 370 in one file may store content or data that all represent the same genome sequence, but each table in the array may represent that content or data in a different resolution.

The system processor 110 may process and store the information in the file tables 370 in various ways. For example, the processing may be performed to generate single-dimensional tables and/or multidimensional tables. All of the tables in a given standardized file may be of the same type or may include a combination of types, e.g., may include both single-dimensional and multidimensional tables. In a genomic annotation application, the single-dimensional tables may include, for example, genome annotation data or quantitative browser tracks, and the multidimensional tables may include, for example, variant call data and gene expression data for one or more samples. In one embodiment, the single-dimensional tables may include multiple attributes.

Figure 8:
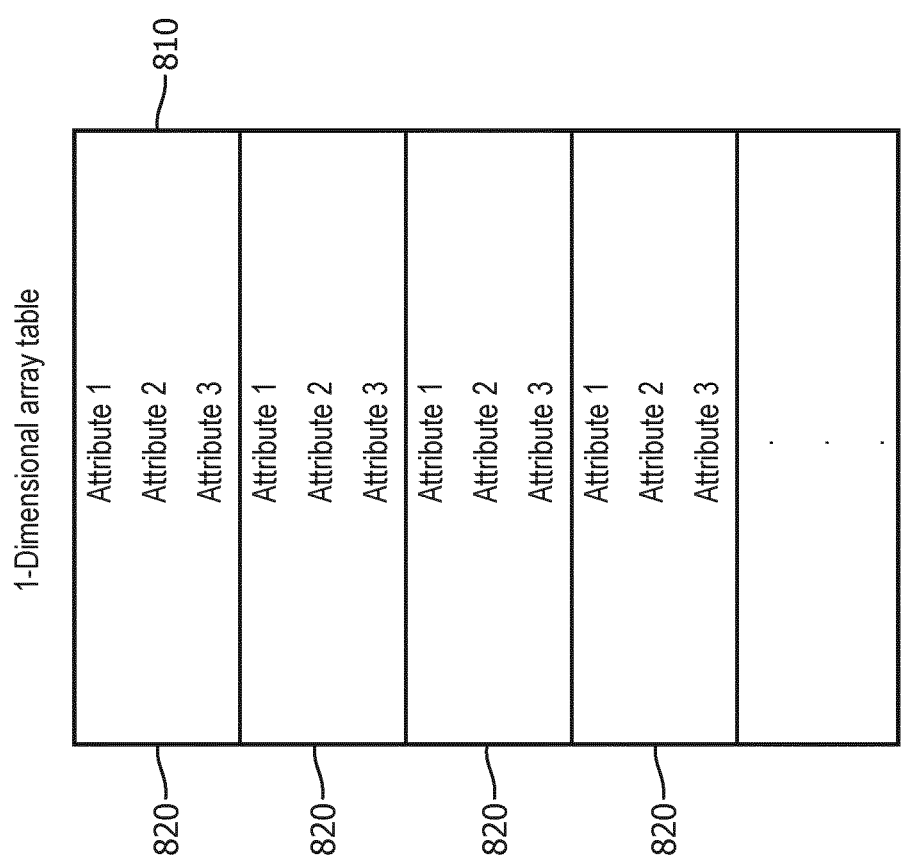
FIG. 8 illustrates an embodiment for processing information for a one-dimensional array.

FIG. 8 illustrates an example of a table that stores data in a one-dimensional array 810 of cells. Each cell 820 in the array includes a plurality of attributes labeled Attribute 1, Attribute 2, and Attribute 3. While each cell in the table has the same number of attributes, the number of attributes in the cells of the table may be different in some embodiments. Examples of the table structure and how the system processor may process the contents for inclusion in that structure are discussed in greater detail below.

Figure 9:
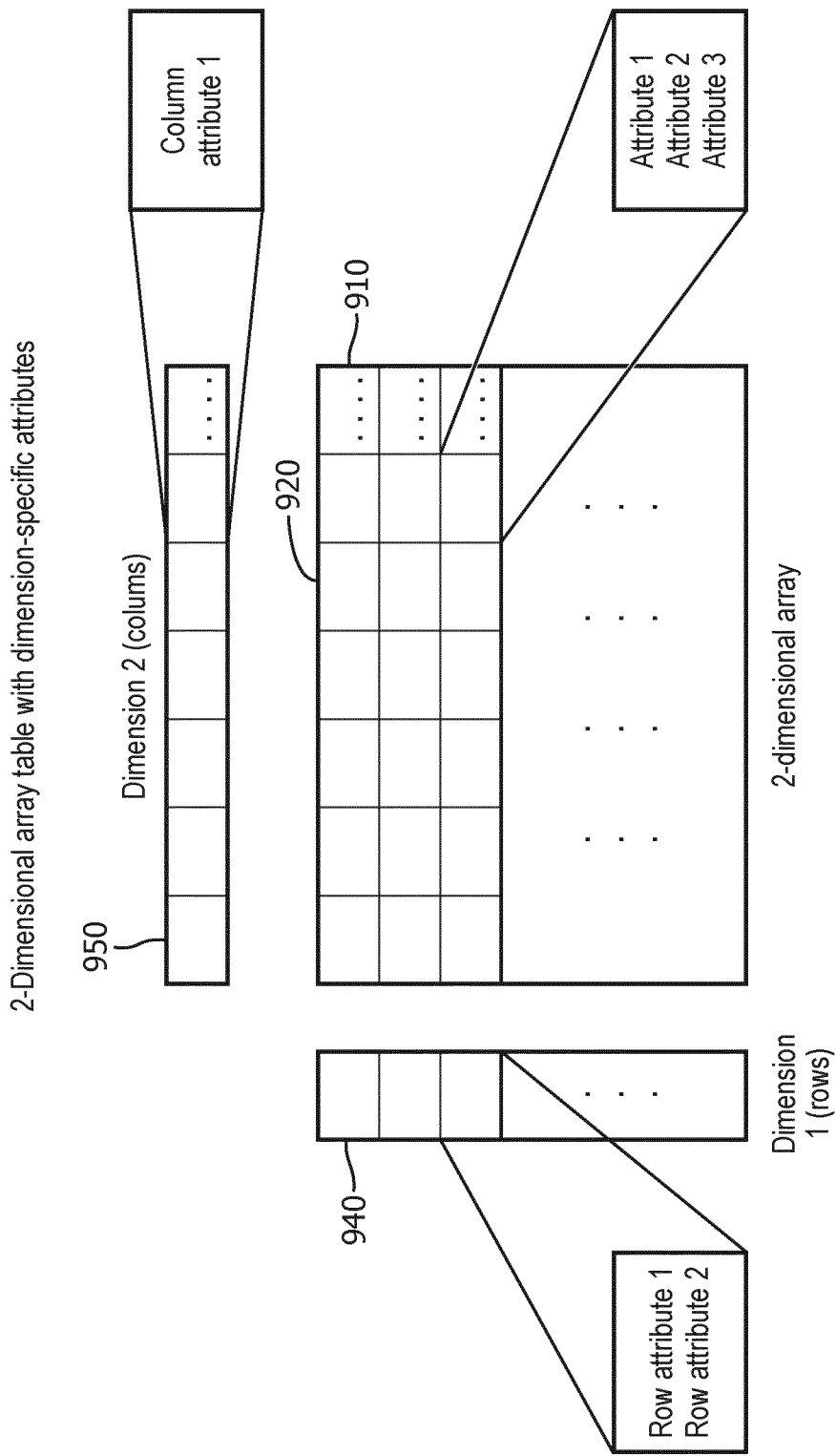
FIG. 9 illustrates an embodiment for processing information into a two-dimensional array with arrays for dimension-specific attributes.

FIG. 9 illustrates an example of a multidimensional table which stores data in a two-dimensional array 910 of cells. Each cell 920 in the table includes one or more attributes corresponding to the data. The number of attributes in the cells may be the same or different. Examples of the table structure and how the system processor may process the contents for inclusion in that structure are discussed in greater detail below.

In one embodiment, one or more of the multidimensional tables 370 in each file may store dimension-specific attributes in addition to the two-dimensional array 910. An example arrangement for storing the dimension-specific attributes is also illustrated in FIG. 9. Here, along with the attributes stored in the array 910, the table 370 stores dimension-specific attributes in two additional tables. A first array 940 of dimension-specific attributes includes cells storing row attributes. A second array 950 of dimension-specific attributes includes cells storing column attributes. Each array 940 and 950 may therefore be thought of as being part of an additional 1-dimensional table in table 370. One example of table 370 that includes these features contemplates representing variant data for multiple samples in the 2-dimensional array table 910, with the sample genotypes and sample-level likelihoods being attributes for each cell in the 2D array. Additionally, array table 940 may store a dimension-specific attribute corresponding to variant position and array table 950 may store a dimension-specific attribute corresponding to sample name. Examples of this table structure and how the system processor may process the contents for inclusion in that structure are discussed in greater detail below.

Figure 10:
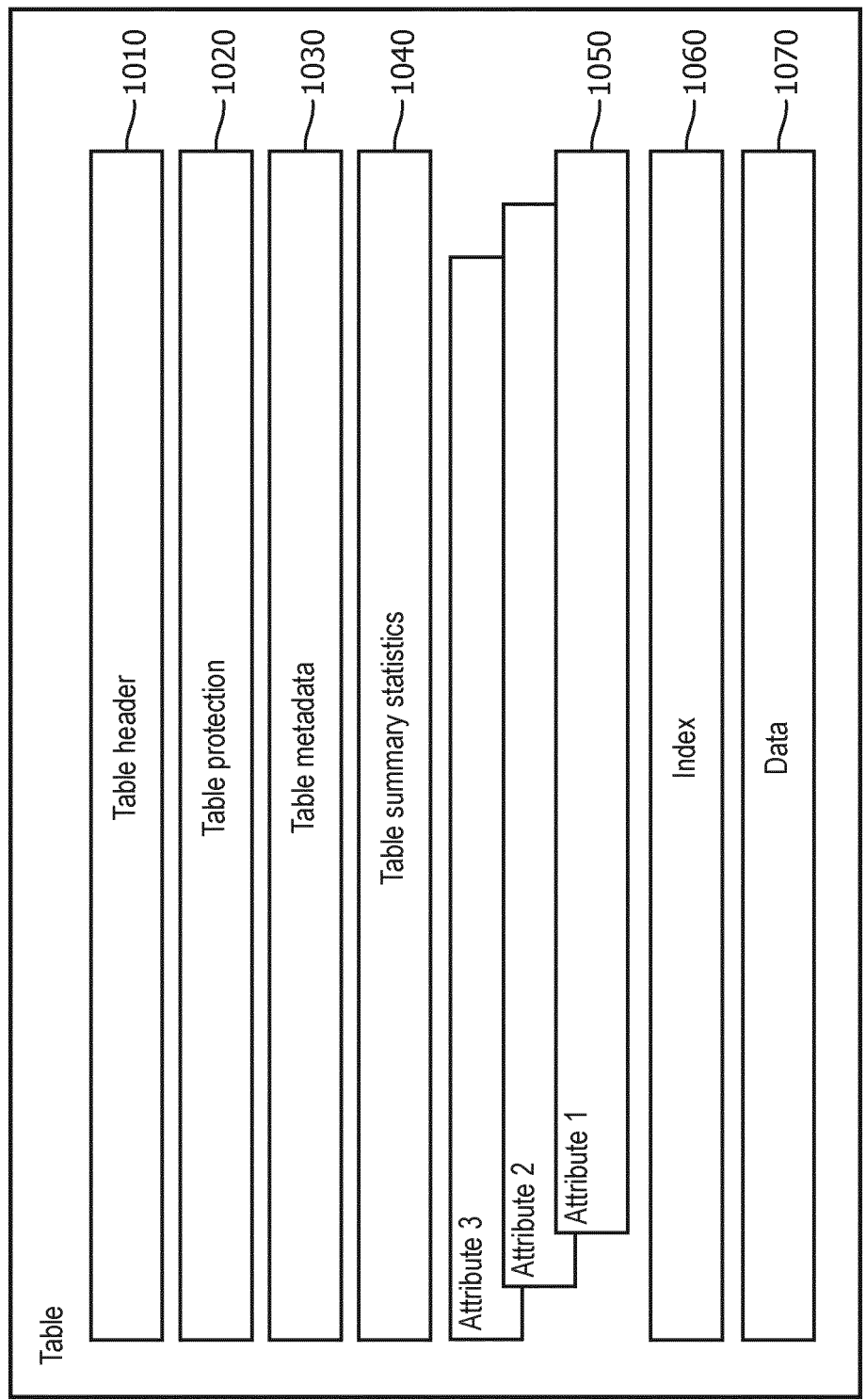
FIG. 10 illustrates an embodiment for processing attribute information that is indexed for the genomic annotation data.

FIG. 10 illustrates an embodiment of how the system processor 110 may process the genomic annotation data into a particular table format. FIG. 11 illustrates an embodiment of the table format for the information processed to generate the table.

Referring to FIGS. 10 and 11, the table format includes a number of sections analogous to the sections in the unified, standardized file format. For example, the table format may include a table header section 1010, a table protection section 1020, and a table metadata section 1030. The table header section 1010 may include a TableID field 1105 indicating the name of the table and a TableInfo field 1110 indicating payload (data) type and/or other information. The table protection section 1020 may include information indicating an access control policy of the table. The table metadata section 1030 may include linkage, traceability and/or other information.

In addition to these features, the table may include a summary statistics section 1040, an attributes section 1050, an index section 1060, and data section 1070. The summary statistics section 1040 may include information indicating averages, counts, distributions, and/or other information relating to the data/attributes stored in the table, which may correspond to one or more key values. The statistics may be used, for example, to enable fast access of the relevant statistics. This information corresponds to reference numeral 1140 in FIG. 11.

The attributes section 1050 may store various attributes for one-dimensional and/or multidimensional array tables as described herein, with or without specific-dimension attributes. For example, if dimension-specific attributes are included in the table, section 1050 may include fields 1150 that indicate the size, name, and metadata for each dimension i (where i=1, . . . , N, with N≥2) and the dimension-specific attributes that correspond to each dimension, as indicated in the table. For 2-dimensional data, the SymmetryFlag field may also store information denoting whether the dimension array is symmetric, e.g., Hi-C data which is symmetric.

The table may include an nAttributesMain field 1160 to indicate the number of attributes in the main array (or two-dimensional array), followed by attribute information for each attribute. The attribute information may include the content and structure described in greater detail herein. In addition, field 1160 may include byte offset information of the attributes/data of the 2D array table. Selective compression of the attributes based on different algorithms, and the byte offset corresponding to the attributes, may allow the attributes (e.g., specific sections of the genomic annotation data) to be selectively accessed during decompression without having to decompress other attributes, table sections, or other data included in the unified, standardized file. The index section 1060 may store an index as described in greater detail herein, and the data section 1070 may store data including for example the chunks or chunk groups as described herein.

FIG. 12 illustrates an embodiment of how the system processor may process the genomic annotation data to generate the attribute information and its associated structure that may be included in the tables or other sections of the unified, standardized file.

Referring to FIG. 12, the attribute information may be processed into a structure that includes an AttributeInfoSize field 1205, an Attribute ID field 1210, an AttributeName field 1215, an AttributeMetadata 1220 field, and an Attribute Type field 1225. The AttributeInfoSize field may include information indicating the size of this information, allowing this structure to be skipped by the processor. The Attribute ID field may include a unique identifier for the attribute. The AttributeName field may include information indicating a name for the attribute, and the Attribute Metadata field may include information for linking or grouping the attribute with one or more other attributes.

The Attribute Type field 1225 may include information identifying the attribute as being one of two types. The first type is a fundamental type and indicates whether the attribute corresponds to a character, string (null terminated), float, double, Boolean, signed and unsigned integers with different bit-widths. The second type is a derived type and indicates whether the attribute corresponds to variable length or fixed length arrays.

In addition to these features, the attribute information structure may include a DefaultValue field 1230, a Summary Statistics field 1235, and a CompressorID field 1240. The DefaultValue field indicates whether most values of the attribute are equal to a predetermined default value. If so, then a predetermined type of encoding (e.g., sparse encoding) may be used for encoding at least the corresponding attribute in the file. The summary statistics field may include information indicating averages, counts, distributions and/or other statistical data that may allow for fast analysis of the attribute.

The Compression ID field 1240 includes information indicating the type of compression algorithm to be used for the attribute. This information may identify, for example, one of the compressors 1611, 1612, . . . , 161N assigned to compress the attribute. This information controls which decompression algorithm is to be used to recover the attribute when retrieved by the system processor in compressed form. If the compressor uses side information/context during the decompression process, the corresponding dependency attributes may also be specified in the attribute information. In the case of multidimensional arrays, the side information may either be obtained from the multidimensional array attributes or from a dimension-specific attribute. For example, in a VCF file, a variant specific field (e.g., a dimension-specific attribute) may be used as side information for compression of genotype data (which is an attribute of 2-dimensional array table). In one embodiment, the system processor may process the attribute information to include additional data required for decompression, which, for example, may be common to all chunks, in the variable CompressorCommonData. This additional data may be useful for storing codebooks, dictionaries, or statistical models computed from the all or a portion of the genomic annotation data files. The chunks and their associated processing is described in greater detail below.

Compressors

The information (e.g., attributes, data, and other information) received by the compression manager 160 may be selectively compressed using, for example, the different compressors 1611, 1612, . . . , 161N of the system indicated in FIG. 1. A non-exhaustive list of these compressors includes:

Run Length Encoding. This compression algorithm may be used, for example, for long runs with same value, and may involve performing a replacement operation based on the value and length of run.

Delta Encoding. This compression algorithm may be used, for example, for increasing sequences of numerical values and may involve a replacement operation that is based on the difference between consecutive values.

Dictionary-Based/Enumeration. This compression algorithm may, for example, be used for attributes having values corresponding to a small set of options. In this case, the algorithm may perform a replacement operation based on an index in the set and may store the resulting dictionary in the CompressorCommonData field.

Sparse: This compression algorithm may be used, for example, to compress attributes that rarely (e.g., less than a predetermined value) differ from the default value, for example, as specified in the attribute information of FIG. 12). This type of compression may involve representing the attribute as a coordinate position and value for the non-default values. The coordinate positions can be further delta coded within each chunk to improve compression, for example, in a 2-dimensional sparse array, the row index can be delta coded and the column index can be delta coded within each row.

Variable Length Array: This compression algorithm may be used, for example, to separate variable length arrays into value streams and length streams.

Tokenization: This compression algorithm may be used, for example, for structured string attributes and may involve splitting the attributes into tokens of different types and encoding each token based on a previous value (e.g., match with previous token, delta, new value, etc.).

General Purpose Compression/Entropy Coding Methods. These type of compression methods include, for example, gzip, bzip2, 7-zip, adaptive arithmetic coding, and other lossless data compression including but not limited to the lossless block-sorting compression of BSC.

The list of compression algorithms indicated above is not intended to be an exhaustive list. In one embodiment, one or more specialized or customized compression algorithms may be included in addition to or in place of one or more of the above-noted compressors. One example of such a specialized compression algorithm is GTC (GenoType Compressor) may be used for compressing variant call data. Such a compression may support fast random access to information contained in the rows/columns of the compressed tables. In some cases, portions of the file may not be compressed, for example, to allow for faster selective access.

One or more of the compressors 1611, 1612, . . . , 161N may produce multiple streams. One example is the sparse compressor which generates coordinate and value streams. In one embodiment, these streams may be compressed using, for example, different entropy coders that are implemented using appropriate specified parameters. Consider, for example, the following.

```
CompressorNameList =      ['sparse','gzip','7-zip']
CompressorParameterList = [
{"outStreams": ["coordinate", "value"]},
{"inStreams" : ["coordinate"]},
{"inStreams" : ["value"]}
]
```

In this case, gzip compression may be applied to the coordinate stream and 7-zip may be applied to the value stream (e.g., JSON may be used to represent the parameters). This enables the application of compressors for each data stream that may produce a predetermined or optimal result. If the streams are not specified, the same compression method may be applied to all the incoming streams.

As previously indicated, in addition to or in lieu of one or more of the external compressors, the compressed file (processed into the unified, standardized file format) may include one or more embedded compressors. That is, the system processor may process the genomic annotation data to include an embedded compressor executable within the unified standardized file format, preferably with appropriate security protections. In the case of embedded compressors, corresponding decompression executables may be included with the compression parameters, along with digital signature(s) as proof of origin and authenticity to protect against malicious software. For interoperability across different platforms, a standardized virtual machine bytecode may be used for the decompression executable.

Chunks and Indexing

Figure 13:
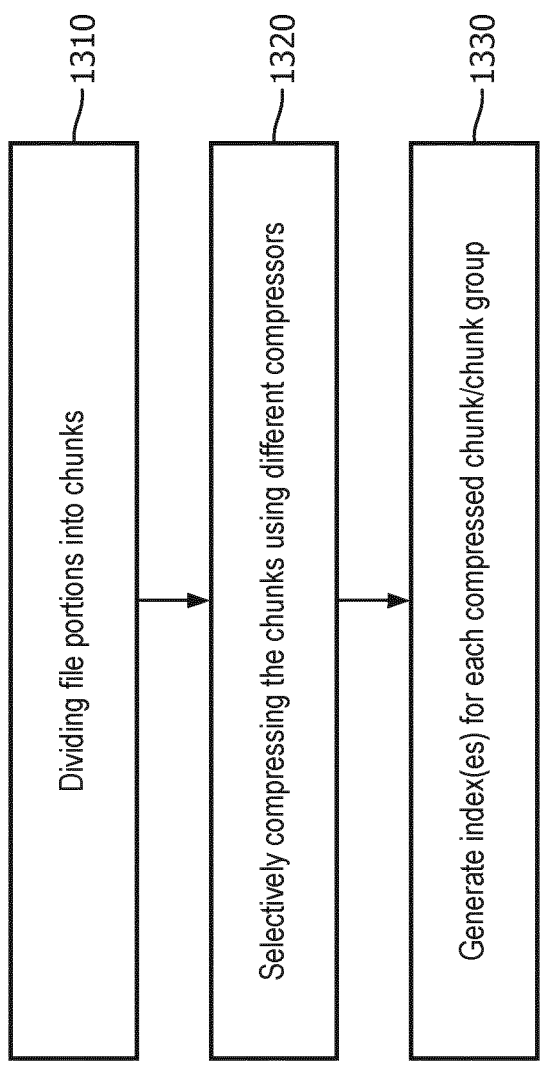
FIG. 13 illustrates an embodiment for selective compression of chunks of data.

FIG. 13 illustrates an embodiment of a method for processing the information arranged in the unified, standardized file format. In this method, the compressed file is processed in a manner that will allow efficient random access to the compressed information during decompression and information recovery.

Referring to FIG. 13, the method includes, at 1310, dividing the attributes, data, (1D and/or 2D) tables, and/or other information in each table 370 (or the entire file) into chunks. The chunks may all be of the same fixed size or may be variable sizes, with an option to use the same chunks for all attributes or not. In one embodiment, the attributes in each table 370 are divided to rectangular chunks in order to allow efficient random access.

At 1320, once divided, the chunks are selectively compressed by different ones of the compressors (for example, as indicated by the instructions executed by system processor 110).

At 1330, the processor then generates at least one index for each compressed chunk or chunk group to be included in the compressed file in the unified, standardized format. The index may include information for efficiently determining the position of each specific chunk in the compressed file. Processing the data into an index may allow for fast access to any given position in the data, by only selectively decompressing the corresponding chunk and without decompressing other chunks that are unrelated or irrelevant to the chunk(s) of interest. To support fast random access based on the values of certain attributes, the system processor may also process the data to generate attribute-specific indexes. In one embodiment, each compressed file may also include information that allows for sharing of codebooks or statistical models for performing decompression across multiple chunks.

Figure 14:
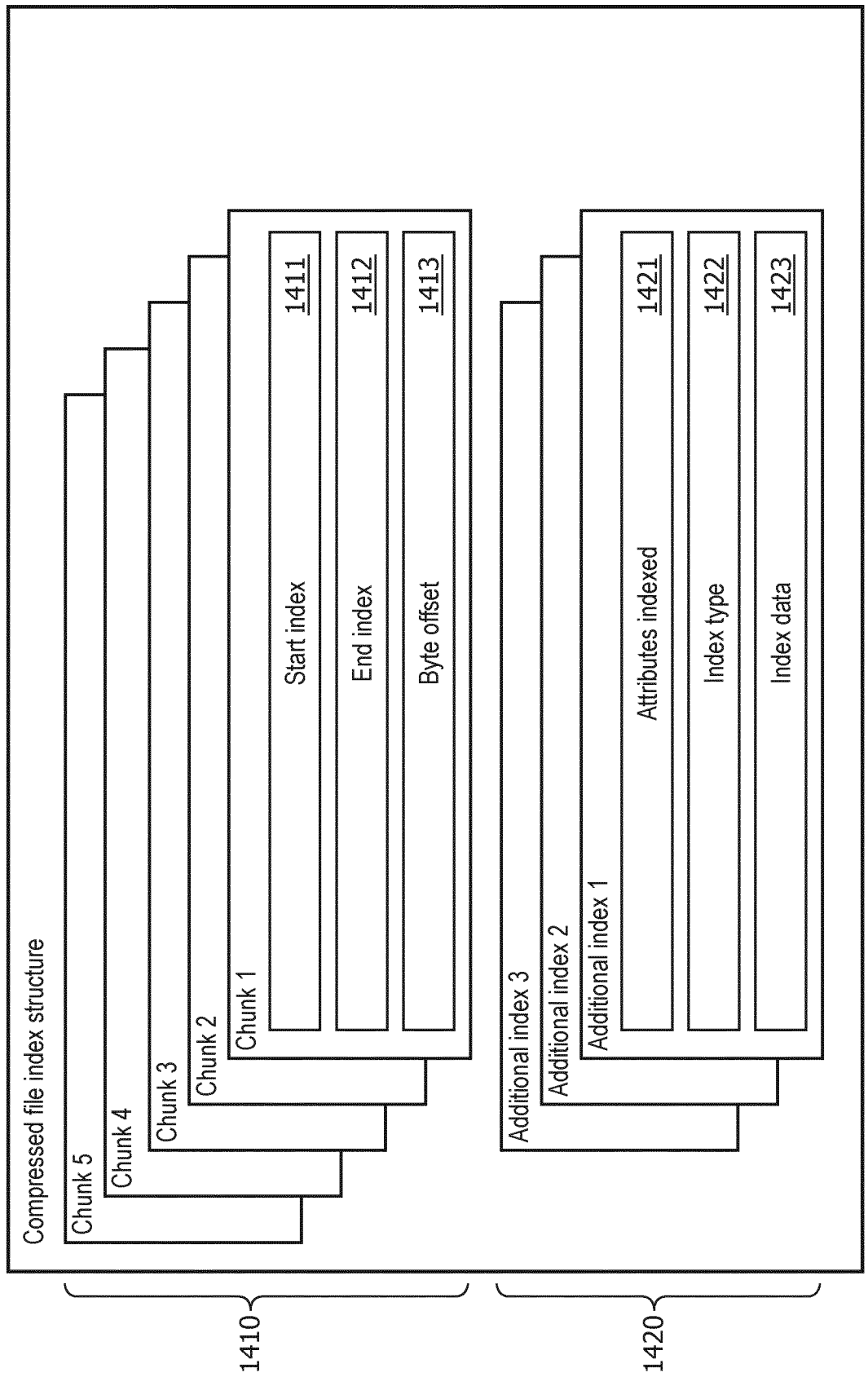
FIG. 14 illustrates an embodiment for processing compressed file index information.

FIG. 14 illustrates an example of an index structure generated by the processor. This example corresponds to an index structure for a one-dimensional table when the flag AttributeDependentChunks field is false, as discussed below. The index includes a first section 1410 and a second section 1420. The first section 1410 includes information corresponding to a plurality of chunks, and with each chunk including start index information 1411, end index information 1412, and byte offset information 1413. The second section 1420 includes a plurality of additional indexes for attributes included in the chunks or other portions of the associated compressed file. Each of the additional indexes may include attributes indexed information 1421, index type information 1422, and index data information 1423. The index file structure may be included, for example, in the index section of each table (for example, as depicted in FIG. 10) or selected tables of the compressed unified, standardized file.

FIG. 15 illustrates an example of the index structure and FIG. 16 illustrates an example of the chunks structure that may correspond and better explain the index structure of FIG. 14, in accordance with one or more embodiments.

Referring initially to FIG. 16, the chunks structure may include an nChunks field 1605 and a VariableSizeChunks field 1610. The nChunks field 1605 includes information (e.g., an integer) indicating the number of chunks corresponding to a particular attribute. The VariableSizeChunks field 1610 includes a flag indicating whether the nChunks are of the same fixed size or varying sizes. While fixed size chunks are simpler to process (especially when included in multidimensional array tables), variable size chunks may be useful, for example, when the sparsity of the data is highly varying and thus where choosing a fixed chunk size is not optimal. In some cases, variable size chunks may be more suitable for a particular attribute of the genomic annotation data (e.g., chromosome, genome position, etc.) and thus may allow faster random access with respect to those attributes.

When the chunks structure indicates that variable-size chunks are used, the following information may be included in the chunks structure: a start index 1615 and an end index 1620 for each chunk along each dimension. This information is also indicated in the compressed file index structure of FIG. 14. In case of fixed-size chunks, the chunk size may be indicated along each dimension. In either case (fixed or variable size), byte offset information 1625 may be included in the file for each chunk in order to allow for random access.

Figure 17:
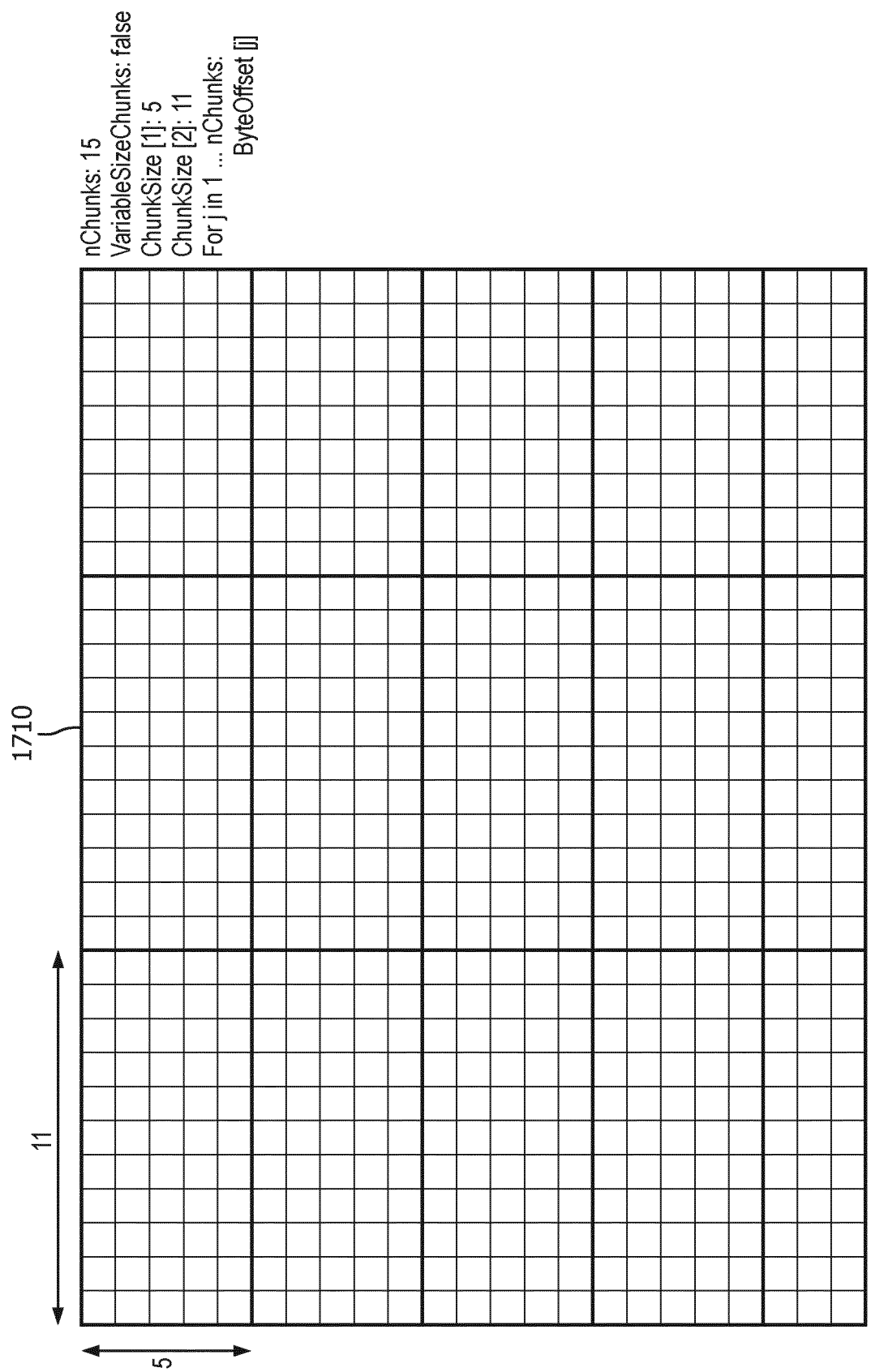
FIG. 17 illustrates an embodiment for generating fixed-size chunks.

FIG. 17 illustrates an example of a portion of a genomic annotation data file pertaining to a particular attribute. In this example, the data is arranged in a two-dimensional array and has been divided into the same fixed-size chunks 1710 (e.g., ChunkSize(1) is 5 and ChunkSize(2) is 11) with a specific ByteOffset[j]. In all, this illustrated portion of data includes fifteen chunks (nChunks=15) and the VariableSizeChunks field indicates a false value for designating the fixed size.

Figure 18:
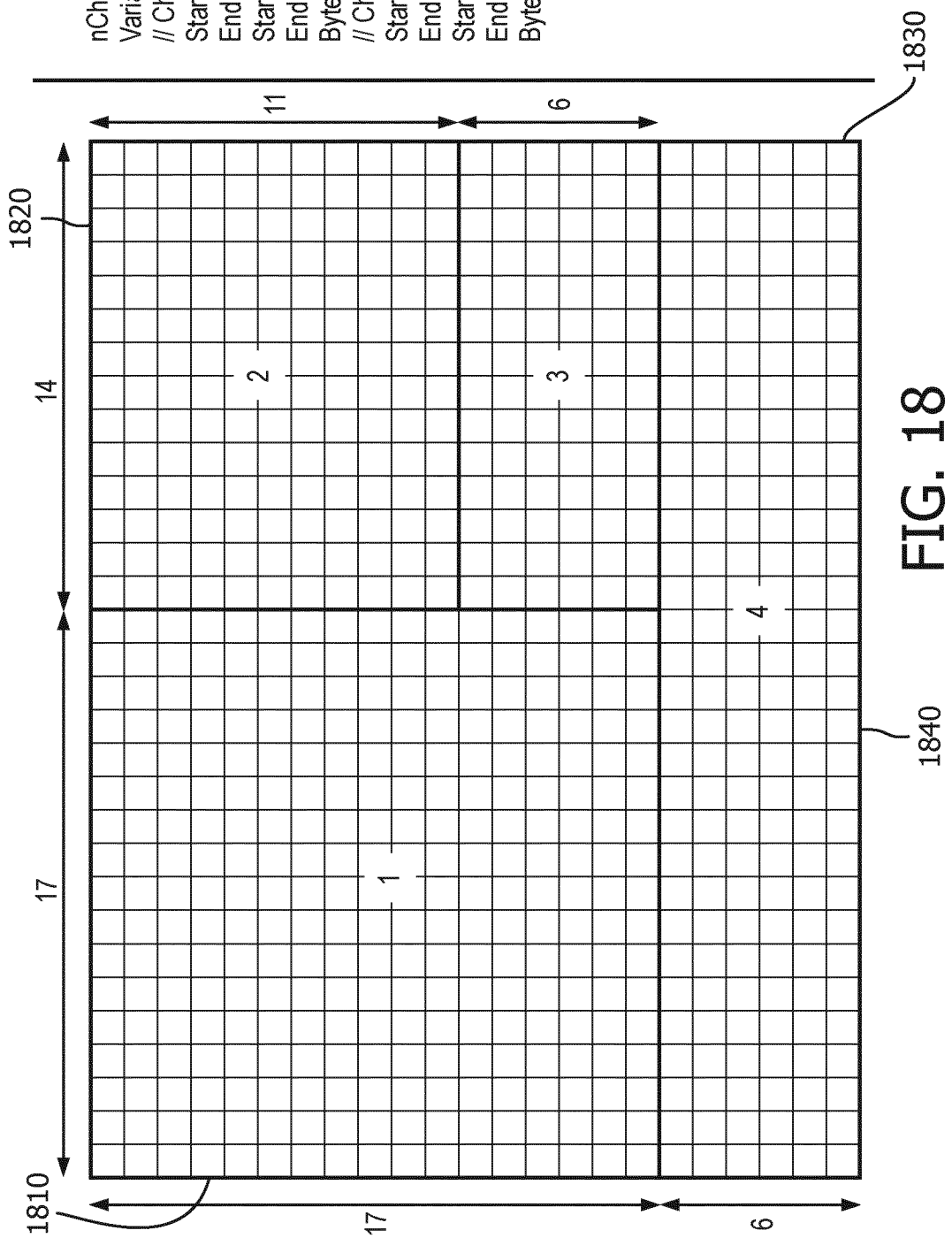
FIG. 18 illustrates an embodiment for generating variable-size chunks.

FIG. 18 illustrates an example of a portion of a genomic annotation data file pertaining to a particular attribute. In this example, the data is arranged in a two-dimensional array and has been divided into variable-size chunks 1810 to 1840. Because the chunk size is variable, a start index and an end index is provided for each block along with an associated ByteOffset. For example, Startindex[1][1]=1 and Endindex [1] [1]=17 are indicated for a first direction of the first rectangular chunk (chunk 1) and Startindex[1][2]=1 and Endindex[1][2]=17 are indicated for a second direction of the rectangular first chunk. Corresponding ByteOffset information is also provided for chunk 1. Similarly, Startindex [2][1]=1 and Endindex[2][1]=11 are indicated for the first direction of the second rectangular chunk (chunk 2) and Startindex[2] [2]=18 and Endindex[2] [2]=31 are indicated for the second direction of the second rectangular chunk. In all, this illustrated portion of the data includes four chunks (nChunks=4) and the VariableSizeChunks field indicates a true value for designating variable size. The remaining chunks 3 and 4 may be specified in a similar manner. The information corresponding to all four chunks for the attribute may be incorporated into the chunk structure, index structure, corresponding tables, and/or other information associated with the unified, standardized file for the genomic annotation data.

Referring again to FIG. 15, the index structure includes information including an AttributeDependentChunks field 1510. This field may include a flag indicating whether chunk sizes are dependent on one or more attributes or if the same chunking (e.g., same chunk sizes) is used for all attributes associated with the file. If the flag has a first value, then, at 1515, the same chunking is used for all attributes. Using the same chunking for all attributes significantly reduces the size of the index structure and may be useful, for example, when most of the time all attributes within a chunk are queried.

Figure 19:
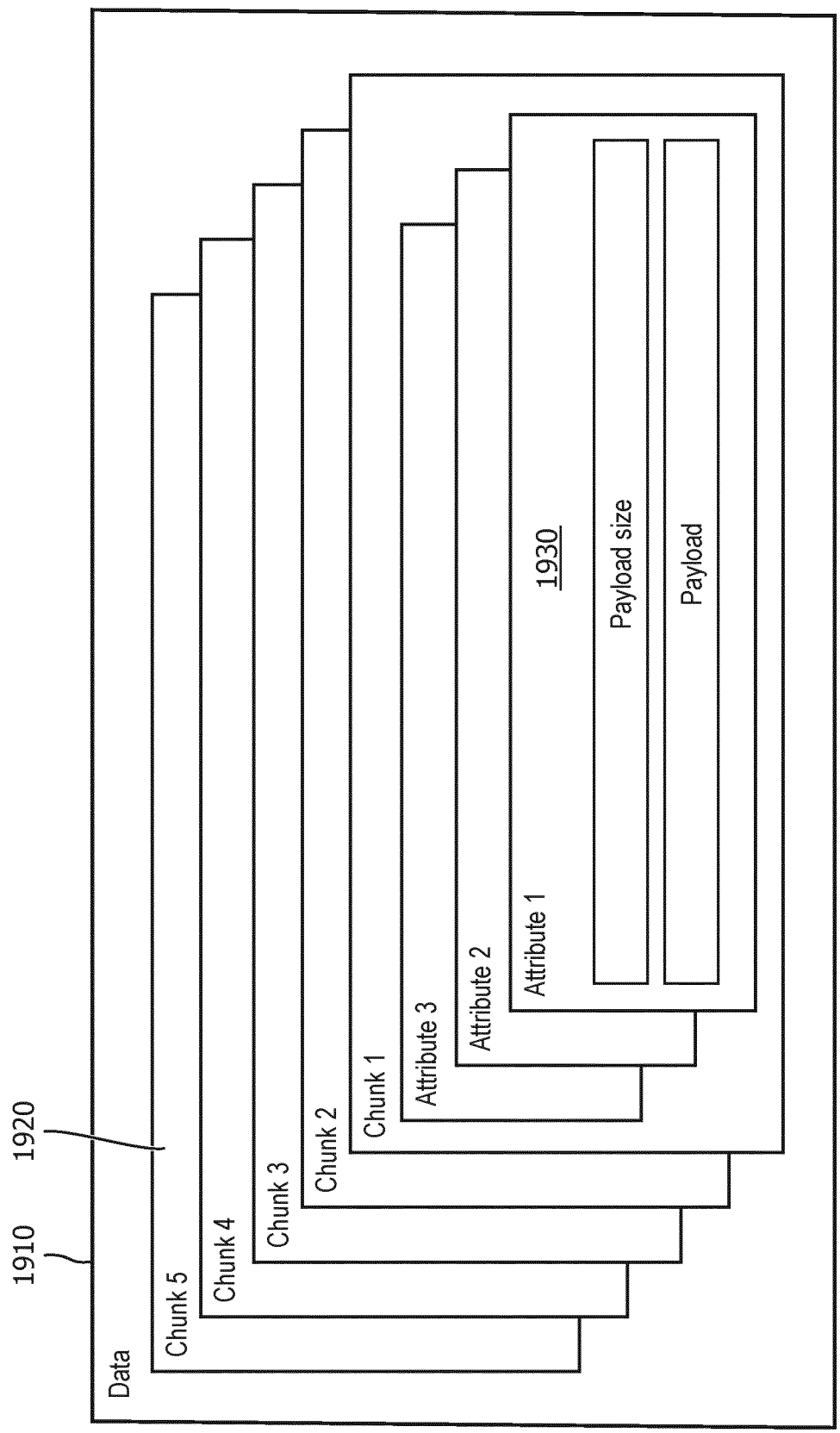
FIG. 19 illustrates an embodiment for processing chunk and attribute information.

An example of the information included in a data payload structure for a one-dimensional case is illustrated in FIG. 19 when the AttributeDependentChunks flag has the first value (e.g., false). In this example, the data 1910 is divided into a plurality of chunks 1920 (e.g., nChunks=5), with each chunk corresponding to one or more attributes 1930. In this case, Chunk 1 corresponds to three attributes. Additionally, each attribute includes information indicating payload size and the payload.

Referring again to FIG. 15, if the flag has a second value, then, at 1520, attribute-dependent chunking is used in the manner indicated in the chart of FIG. 16. Attribute-dependent chunking may be useful, for example, when the optimal chunk size for different attributes with respect to compression and random access varies significantly (e.g., more than a predetermined value). For example, if some attributes are sparse and others are dense, using the same chunk size might lead to suboptimal compression. Attribute-dependent chunking may also be useful when all chunks for a single attribute are queried on a frequent basis, e.g., more than a predetermined frequency value.

Figure 20:
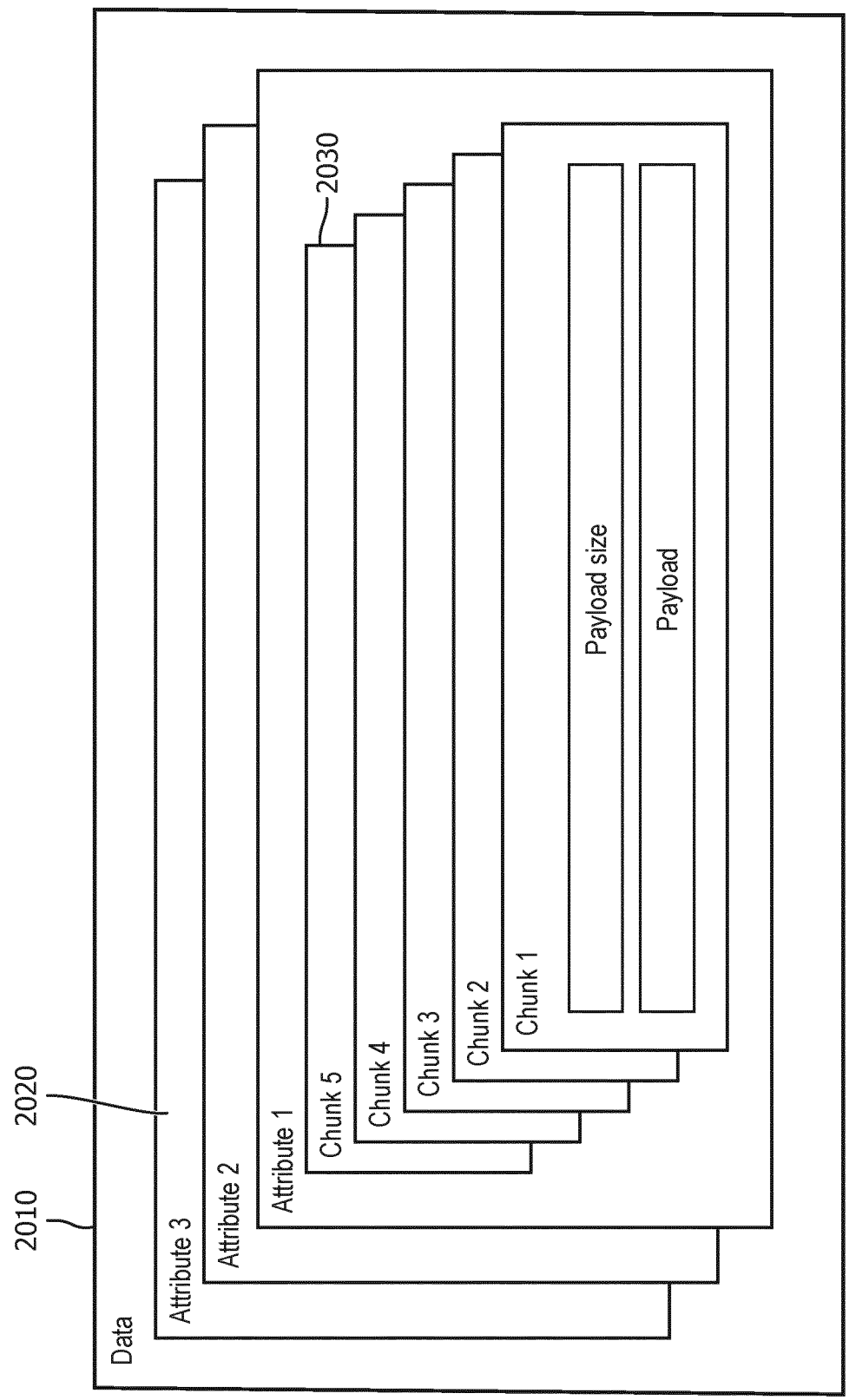
FIG. 20 illustrates an embodiment for processing chunk and attribute information.

An example of a data payload structure for a one-dimensional case when the AttributeDependentChunks flag has the second value (e.g., true) is illustrated in FIG. 20. In this example, the data 2010 corresponds to one or more attributes 2020. Each attribute includes or corresponds to one or more chunks 2030 into which the data is divided. Additionally, each chunk includes information indicating payload size and the payload. As is evident from a comparison of FIGS. 15 to 20, in accordance with one embodiment the organization of the chunks and attributes depends on the mode of operation, e.g., whether or not attribute-dependent chunking is performed.

In one embodiment, random access during a selective decompression process may be performed without using row and/or column numbers. This embodiment may be performed, for example, for applications where random access is performed with respect to certain attributes, e.g., where random access is performed with respect to genome position.

In these cases, the index structure of FIG. 15 may include one or more attribute-specific indexes 1525. For example, when attribute-dependent chunking is performed, nAdditionalIndexes may be used, where n≥1. The attribute-index(es) may be included in the index structure to achieve faster querying on an attribute(s)-basis, instead of on a row/column basis. For example, in the case of genomic annotation data, indexes may be generated by the system processor 110 and included in the index structure of FIG. 15 for the attributes of chromosome and position. When querying is performed by the system processor, the chunk(s) or chunk number(s)) matching the chromosome and position attributes of the query may be returned for selective decompression. Different attributes and/or a different number of attributes may be used in other embodiments.

The index structure may also include other information relating to the nAdditional indexes. For example, for each attribute-specific index, the index structure may include an AttributeIDsIndexed field 1530, an IndexType field 1535, an IndexSize field 1540, and an IndexData field 1545. The AttributeIDsIndexed field 1530 may include a list of the one or more attributes that have been indexed, e.g., chromosome, genome position, etc.

The IndexType field 1535 may include information indicating the type of indexing performed for each attribute listed in the AttributeIDsIndexed field. In one embodiment, the type of indexing for one or more of attributes may be different from a standard set. For example, an R-tree or CSI index may be used for each of the chromosome attribute, the genomic position attribute, and for range queries. A B-tree index may be used for database-type queries. The genomic range indexing can store the leftmost and rightmost coordinate for each chunk, allowing quick identification of the chunks overlapping the queried range. Similarly, the B-tree index can store a map from the attribute value to the chunk containing the value and the position of the value within the chunk.

The IndexSize field 1540 may include information indicating the size of the index generated by the system processor for each listed attribute.

The IndexData field 1545 may include the actual indexing data in a predetermined (e.g., binary format). The type of format may depend, for example, the type of index generated for the attribute.

FIG. 21 illustrates example logic which may be executed by the system processor 110 to generate the payload information, for example, as indicated in the data of FIG. 19 and/or FIG. 20. This logic is implemented based on the value in the AttributeDependentChunks field. More specifically, as is evident from a comparison of FIGS. 19 and 20, the structure of the payload is different for different values of AttributeDependentChunks field. When the chunks of data for the payload are not attribute-dependent, then the system processor implements logic to generate the structure illustrated in FIG. 19 as previously described. When the chunks of data for the payload are attribute-dependent, then the system processor implements logic to generate the structure illustrated in FIG. 20 as previously described.

Figure 22:
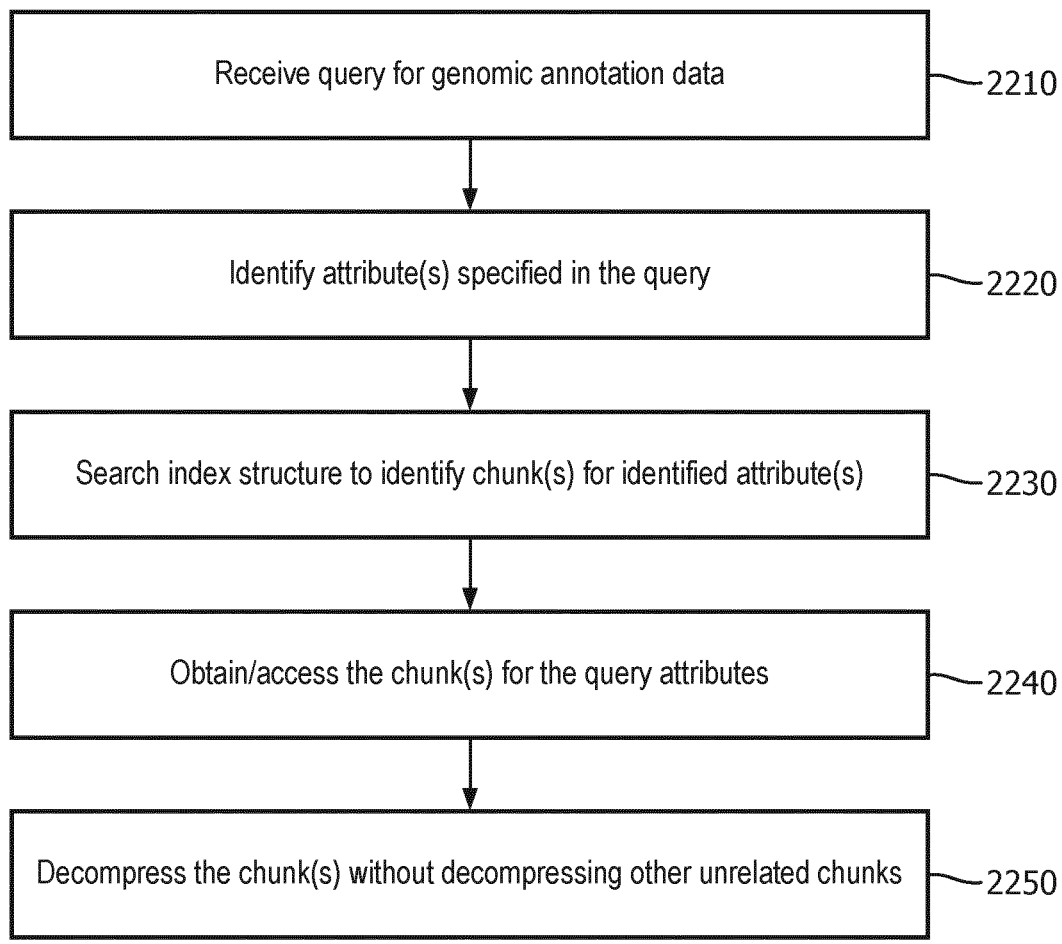
FIG. 22 illustrates an embodiment for selectively decompressing genomic annotation data in a unified, standardized format.

FIG. 22 illustrates an embodiment of a query method that may be performed by the system processor 110 for purposes of selectively identifying and decompressing the annotated genomic data based on an index structure, such as but not limited to the index structure of FIG. 15. The query may be performed based on a lookup operation implemented as follows. Initially, at 2210, the system processor 110 receives a user query that includes information indicating one or more attributes of interest. At 2220, the system processor parses the query and identifies the one or more attributes in the query. The attribute(s) may be specified in the query in various ways, e.g., a string such as "abcd" or a specific attribute number within a range of numbers identifying respective attributes. At 2230, the system processor searches the attribute-specific indexes to determine the chunk(s) or chunk number(s) corresponding to the attributes identified in the query. At 2240, the system processor searches the genomic annotation data to retrieve (or otherwise gain access to) the chunk(s) or chunk number(s) that match the query attributes. The chunks may be recovered using the chunk index to filter out values that match the condition (because chunks may also contain non-matching values).

At 2250, the recovered chunks may be selectively decompressed (e.g., decompressed without decompressing other chunks unrelated to the specified attributes). The selective decompression is made possible because the chunks of data were previously selectively compressed independently from one another. Decompression may be performed based on the algorithms indicated in the attribute information structure of FIG. 12, and/or the indexes, tables, or other structures described herein. In the event that the chunks were subject to global compression, the global compression data may be shared across chunks, for example, using the CompressorCommonData mechanism indicated in the attribute information structure. In one embodiment, for symmetric two-dimensional array tables (e.g., the SymmetryFlag in the table of FIG. 11 is true), the chunks may only cover a portion, e.g., a lower triangular part and the diagonal. In this case, the decompression process may take care of the upper diagonal values by filling in the corresponding lower triangular values. For other cases, the chunks may cover the entire range of indices without overlapping.

Interoperability

The unified, standardized file format for the genomic annotation data may have various additional features. One additional feature relates to linkages and interoperability associated with the files generated in this format. In one embodiment, the system processor may process the file information into the unified, standardized format, as described herein, to be independent from any encoding or formatting of the source files, e.g., the data as provided by the data source 140 of FIG. 1.

In another embodiment, the system processor may process the file information into the unified, standardized format to be linked and interoperable with the encoding and/or formatting of the source files. The data source files may be in an MPEG-G format/encoding or another type of format or encoding.

When processed into a linked and interpretable state, the file may be processed to be part of the source files (e.g., MPEG-G file) by storing the associated information in a dataset. An MPEG-G file can store the data for an entire study, with each dataset group corresponding to a different individual. Each MPEG-G dataset group is further divided into datasets corresponding to different sequencing runs.

For storing the data corresponding to a single individual, different annotation files may be incorporated as distinct datasets, with each dataset including a single annotation file or sequencing data. An example of the distinct datasets is set forth below.

Dataset group (single individual)→
    Dataset 1 (sequencing data)
    Dataset 2 (sequencing data)
    Dataset 3 (variant call data)
    Dataset 4 (gene expression data)

For collecting annotation data from a large study, the datasets may be organized as follows:

Dataset group (large study)→
    Dataset 1 (variant call data)→
        Annotation file (sample 1)
        Annotation file (sample 2)
    Dataset 2 (gene expression data)→
        Annotation file (sample 1)
        Annotation file (sample 2)

In one embodiment, the different annotation files may be merged together for improved compression and analysis performance, for example, as indicated below:

Dataset group (large study)→
    Dataset 1 (variant call data)→
        Annotation file (all samples)
    Dataset 2 (gene expression data)→
        Annotation file (all samples)

In order to perform this implementation, the system processor may augment the existing dataset header structure with additional fields in order to support the data type (sequencing/variant/gene expression/ . . . ), number of annotation files in the dataset, and the byte offset of each of these files. When a compressor is shared across annotation files or across datasets, the parameters of the compressor may be stored at the dataset level or dataset group level, respectively. In one embodiment, one or more of the annotation files may include a compressor structure with compressor name "POINTER" and the compression parameter storing the location, e.g., {"DatasetGroupId": 1, "DatasetId": 2, "CompressorId": 5} denotes that the compressor is as specified in the 5th compressor in dataset group 1, dataset 2.

Linkages

In addition to the foregoing features, the system processor may process the data to generate unified, standardized files in a format which includes linkages between different types of annotation data and corresponding sequencing data. In one embodiment, the linkages may be provided based on metadata stored in or in association with the files.

This may be accomplished by the system processor specifying the dataset groups, or datasets storing the sequencing data or the related annotation data, in the FileMetadata field of FIG. 4 or a TableMetadata field using, for example, the URI (uniform resource identifier) notation described in MPEG-G part 3 or by using JSON. For example, to provide linkage to a sequencing dataset, the following JSON may be used in the FileMetadata:

```
"Linkages": [{
    "DataType"       : "Sequencing",
    "DatasetGroup"   : 5,
    "Dataset"        : 2
}]
```

While the above example shows only a single linkage, multiple linkages may be provided in another embodiment.

Additionally, or alternatively, the system processor may generate table-level linkages. In one embodiment, the system processor may generate table-level linkages by index. In this case, for example, the nth row (column) in one table may correspond to the mth row (column) in another table. This type of linkage may avoid repetition when multiple annotation files/tables share the same rows/columns (e.g., multiple VCFs that are not yet merged and consist of the same variants). Similarly, this type of linkage may be useful when the information relating to the samples is stored in a single table, and both VCF and gene expression tables link to this.

In another embodiment, the system processor may generate table-level linkages by value. In this case, a specific attribute may be linked by matching value to an attribute in another table. For example, the gene expression data might include gene names without detailed information about the genes, which is available in another file. An example use case for such a linkage might be a query requesting gene expression data for all genes in the MHC (major histocompatibility complex), which corresponds to autoimmune diseases and specifies a range of coordinates in chromosome 6 for humans. To address this query, the gene names for the coordinate range can be obtained from the gene information file based on a genomic coordinate index and then these names can be queried in the gene expression file to the get the required data. This following example pertains to these features, and specifically may link rows (dimension 1) with rows of another table (e.g., Table No. 3 in same annotation file):

```
"Linkages": [{
    "Type"                      : "byIndex",
    "DimensionInCurrentTable"   : 1,
    "Table"                     : 3,
    "DimensionInLinkedTable"    : 1
}]
```

An example for linking columns (dimension 2) with rows of another table by value of attribute (attribute 2 in dimension 2 of current table linked to attribute 5 in dimension 1 of table 3 in dataset 4, file 2) may be performed by the system processor as follows:

```
"Linkages": [{
    "Type"                      : "byValue",
    "DimensionInCurrentTable"   : 2,
    "AttributeInCurrentTable"   : 4,
    "Dataset"                   : 4,
    "AnnotationFile"            : 2,
    "Table"                     : 3,
    "DimensionInLinkedTable"    : 1,
    "AttributeInLinkedTable"    : 5,
}]
```

Since the metadata structure supports arbitrary information storage, the system processor may extend the linkage even further to link more than 2 tables, for example, by using a standardized format (e.g., Table 3 may translate the gene IDs used in table 1 to the gene names in Table 2). While the examples shown above use a specific JSON-based format for linkages, a different format may be used such as but not limited to XML.

In one embodiment, an attribute-based linkage may be implemented. A metadata-based linkage may be useful for high level linkages, but in some cases linkage for each row/column may be beneficial. For example, in a VCF file with multiple samples, sequencing data corresponding to particular samples may be linked by adding attributes SequencingDatasetGroup and SequencingDataset to the column attributes. Such linkage attributes may have "LinkageAttributeFlag" set to True in the metadata to allow the decompressor to distinguish linkage attributes from normal attributes.

In some cases, the system processor may perform a mapping operation between annotation datasets according to genomic region. This may be achieved, for example, by separately indexing each of the datasets. For example, in order to find the sequencing data corresponding to a region in the VCF file, the master index table of the sequencing data may be accessed to determine the appropriate access unit(s). Using separate indexing for different datasets allows for the choice of predetermined (e.g., optimal) chunk sizes and other parameters for each of the datasets. Furthermore, in some cases direct linking of a variant to an AU might not be possible due to different AU classes. Similarly, in VCF files with multiple samples, variant maps to the access units across several datasets and the storing of this information may take up significant storage. In one embodiment, the AUId or byteoffset in the sequencing data may be stored as a row attribute in the VCF file, allowing quick lookup of the access unit corresponding to the current variant. Also, a gene may be mapped to a list of variants by using a list-type attribute to the genes.

In one embodiment, an access control policy may be specified at the file level (e.g., in the annotation file of FIG. 4), the table level (e.g., in the information of FIGS. 10 and 11), or both, using a predetermined format such as XACML. Certain users might have access to all the data, while others might have access only to coarse resolution data (recall that different resolutions are stored in different tables). This type of policy may be specified at the file level. Policies specific to the attributes within a table may be specified, for example, at the table level. This may include access to only a subset of attributes or access only to certain chunks based on the value of some attribute. Another type of policy may allow access to the metadata and information, but not to the actual data.

Decompression

The processes for decompressing selected portions of a file, or the entire file, in the unified, standardized format described herein may initially involve performing one or more types of queries. The queries and/or decompression algorithms may not be mutually exclusive, and in some embodiments may be combined together. For example, both the metadata and certain attributes may be decompressed or selected attributes from selected chunks may be decompressed. The decompression may be performed by the system processor or another processing entity coupled to the system processor. In some cases, the access control policy may restrict some of these queries. Application programming interfaces (APIs) may be used to support these. Such APIs may be similar to MPEG-G part 3 or may be a different type of API.

Metadata/Information Queries. These types of queries may only query metadata and information corresponding to the tables (e.g., resolution level), compressors, attributes and/or chunks requested. In carrying out the query, first, top-level information as set forth at the beginning of the annotation file of FIG. 4 may be directly accessed. The table-specific metadata/attribute details may be selectively accessed using the ByteOffset of the table of FIG. 4.

Complete Data Decompression. This type of decompression may involve decompression of the entire data, including all tables and attributes. This may be performed by, first, reading the top-level metadata and table information of the file, as previously described. Then, the compression parameters are loaded into a decompression manager. For each table, the table information, dimensions, and attributes are then read, following by reading of the index to determine positions of the chunks along each dimension. The data payloads for each chunk and each attribute are then selectively decompressed, either serially or in parallel. If an attribute is compressed using another attribute as a dependency/context, then decompression may be performed by first decompressing the other attribute. If the attribute uses CompressorCommonData, this information may be loaded before any chunks are decompressed. For two-dimensional symmetric arrays (e.g., see the SymmetryFlag previously discussed), only the diagonal and lower triangular matrix may be decompressed, filling in the upper triangular part using symmetry.

Decompression of Only One Table. This type of decompression is similar to Complete Data Decompression, except that the ByteOffset field in the annotation file (e.g., of FIG. 4) is used to jump to the requested table and only that table is decompressed.

Query for Selected Attributes of a Table. This method is similar to Decompression of Only One Table, except that only the information corresponding to the requested attributes is read. The other attributes are skipped over based on the AttributeInfoSize variable in the attribute information structure of FIG. 12. In one embodiment, only the requested attributes are decompressed by skipping over other attributes based on the Payload Size[i][j] information in FIG. 22. When attribute-dependent chunks are used, all the chunks for a given attribute may be stored together, for example, as set forth in the data payload structure of FIG. 20.

Query Only Selected Range of Indices in an Array. This method is similar to Decompression of Only One Table, except that the index is loaded and, depending on the type of chunking (fixed size/variable size), the chunks overlapping with the requested range are determined. Also, the ByteOffset information in the chunks structure table of FIG. 16 may be used to jump to the payload for the chunks determined above. In some cases, the method may be more efficiently implemented when attribute-dependent chunks are not used and all the attributes for a given chunk are stored together. Also, the requested chunks are decompressed and only the overlapping indices are returned. If the compressor of some attribute allows efficient random access within a chunk, this random access may be utilized as a basis for further boosting decompression speed. Example scenarios of where this might happen include sparse arrays or specialized compressors for genotypes, such as GTC.

Query Based on Value/Range of Certain Attributes. This approach is similar to Query Only Selected Range of Indices in the Array, except that, if an additional attribute-specific index (e.g., indicated in the Index Structure of FIG. 15) is available for the attributes in question, this index is used to determine the relevant chunk(s). If such an index is not available, the attributes in question may be decompressed for all the chunks and the relevant chunks may then be determined. Even when an additional index is not used, decompression speed may be increased because only some attributes for all the chunks are decompressed. In one embodiment, remaining attributes may be decompressed only for the relevant chunks.

Folder Structure and Editing

The processing of genomic annotation data by the system processor into a unified, standardized file format as described above, offers many advantages in terms of efficiency, convenience, reduced system requirements, fast querying, and data accessibility. Additional variations and adjustments of the embodiments may be made in order to better conform to specific applications.

For example, in the case where data is stored on a single machine and is subject to frequent editing, the data may be stored in a directory/folder hierarchy using a file manager. The hierarchy may allow for easy manipulation of parts of the data by modifying only the files corresponding to a single chunk and attribute, rather than having to overwrite the entire file. When the editing is completed and the data is to be transmitted, the file may be converted back to the single file format. This may be performed by recomputing the index based on the data payload sizes and packing the folder hierarchy back into one file.

Figure 23A:
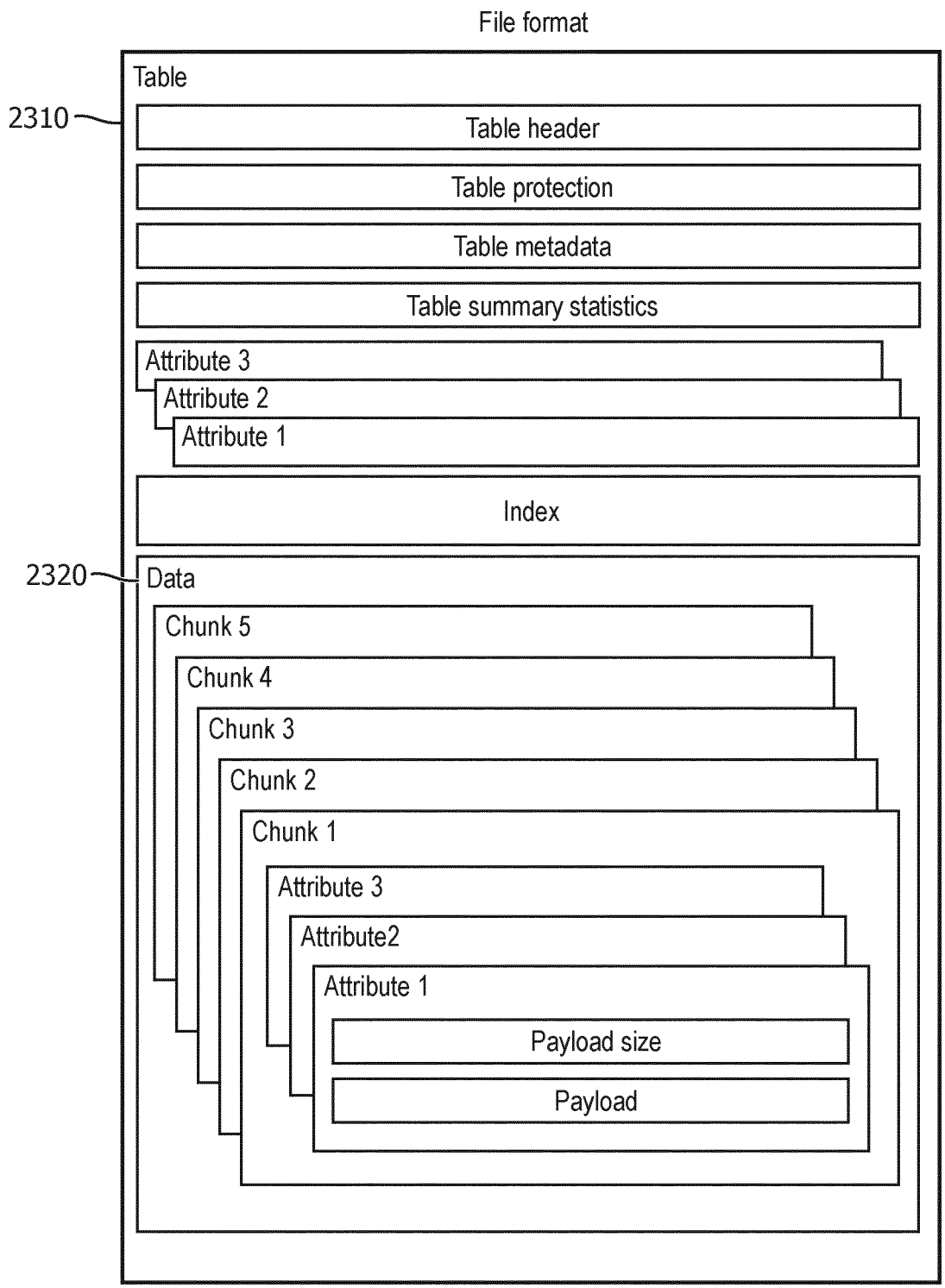
FIGS. 23A and 23B illustrate a method for converting a file format into a folder hierarchy in accordance with one or more embodiments.
Figure 23B:
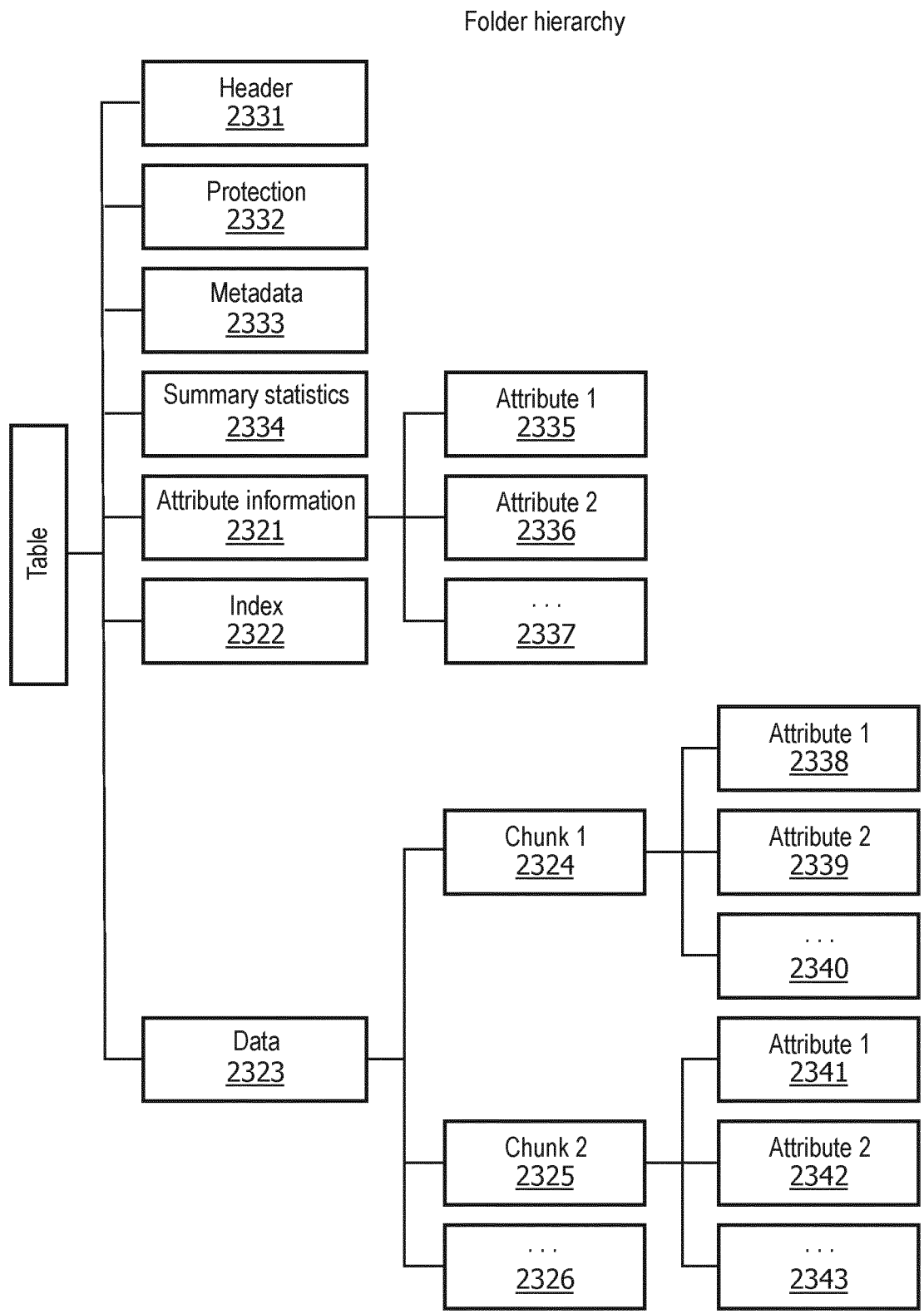

An example is illustrated of how the file format (e.g., FIG. 23A) may be converted to the folder hierarchy (e.g., FIG. 23B) and back for a single table. In this example, the conversion is performed by treating each table in the table section 2310 of the file format as a folder in the folder hierarchy, and each chunk of the data in the data section 2320 of the file format as a folder in the folder hierarchy (e.g., assuming the AttributeDependentChunks field stores a False value). In the folder hierarchy, blocks 2331 to 2343 correspond to files and blocks 2321 to 2326 correspond to folders. In the folder hierarchy, the index only needs to store the attribute-specific indexes since the chunks are already stored in distinct folders. A simple example is shown in FIG. 9.

When considered as a folder hierarchy, the proposed scheme can be roughly related to the scheme proposed in the aforementioned related patent application by the following modification in terminology: "attribute": "region with one or more rows/columns" and "chunk": "block".

To illustrate one or more of the aforementioned embodiments may be implemented, the following two examples are discussed for storing a variety of annotation data while providing relevant functionalities: (1) Variant Call Data and (2) Genome Functional Annotation Data.

Variant Call Data

TABLE 1

A VCF File Example (from IGSR)

```
##fileformat=VCFv4.0
##fileDate=20090805
##source=myImputationProgramV3.1
##reference=1000GenomesPilot-NCBI36
##phasing=partial
##INFO=<ID=NS,Number=1,Type=Integer,Description="Number of Samples With Data">
##INFO=<ID=DP,Number=1,Type=Integer,Description="Total Depth">
##INFO=<ID=AF,Number=.,Type=Float,Description="Allele Frequency">
##INFO=<ID=AA,Number=1,Type=String,Description="Ancestral Allele">
##INFO=<ID=DB,Number=0,Type=Flag,Description="dbSNP membership, build 129">
##INFO=<ID=H2,Number=0,Type=Flag,Description="HapMap2 membership">
##FILTER=<ID=q10,Description="Quality below 10">
##FILTER=<ID=s50,Description="Less than 50% of samples have data">
##FORMAT=<ID=GT,Number=1,Type=String,Description="Genotype">
##FORMAT=<ID=GQ,Number=1,Type=Integer,Description="Genotype Quality">
##FORMAT=<ID=DP,Number=1,Type=Integer,Description="Read Depth">
##FORMAT=<ID=HQ,Number=2,Type=Integer,Description="Haplotype Quality">
#CHROM  POS  ID  REF ALT  QUAL FILTER INFO
FORMAT  NA00001  NA00002  NA00003
20 14370 rs6054257 G A 29 PASS NS=3;DP=14;AF=0.5;DB;H2
GT:GQ:DP:HQ 0|0:48:1:51,51 1|0:48:8:51,51 1/1:43:5:.,.
20 17330 . T A 3 q10 NS=3;DP=11;AF=0.017
GT:GQ:DP:HQ 0|0:49:3:58,50 0|1:3:5:65,3 0/0:41:3
20 1110696 rs6040355 A G,T 67 PASS NS=2;DP=10;AF=0.333,0.667;AA=T;DB
GT:GQ:DP:HQ 1|2:21:6:23,27 2|1:2:0:18,2 2/2:35:4
20 1230237 . T . 47 PASS NS=3;DP=13;AA=T
GT:GQ:DP:HQ 0|0:54:7:56,60 0|0:48:4:51,51 0/0:61:2
20 1234567 microsat1 GTCT G,GTACT 50 PASS NS=3;DP=9;AA=G
GT:GQ:DP 0/1:35:4 0/2:17:2 1/1:40:3
```

Table 1 above shows a section of a VCF file, with 5 variants and 3 samples included. The VCF file may be processed by the system processor 110 into the unified, standardized file format while preserving the data and providing associated additional functionalities. Such a file may have the following features.

Metadata. The comment lines (starting with ##) may be retained as part of the FileMetadata. If this is stored as part of an MPEG-G file with sequencing data, the metadata may also include the corresponding dataset groups that contain the sequencing data corresponding to this variant call data.

Traceability. When traceability information is stored as part of an MPEG-G file with sequencing data, the traceability information may include one or more commands for generating the variant call(s), starting from the raw sequencing data along with the URIs of the tools used and their versions. The traceability information may be used to validate the file in a reproducible manner.

Tables. When variant data is stored in a single resolution, the variant data may be stored in a single table in the unified file format, with nDimensions=2.

Dimensional Attributes. For the first dimension (variants), there may be several dimensional attributes such as CHROM, POS, ID, REF, ALT, QUAL, FILTER, and the INFO fields. The INFO field may be broken into multiple attributes such as NS, DP, AF, etc., as described in the comments. The types of these attributes may also be mentioned in the comment fields. The attribute metadata may be used for grouping these together (e.g., NS, DP, AF may belong to the group INFO). The default value may depend on the attribute, e.g., the default value may be set to "PASS" for the FILTER attribute.

For the second dimension (samples), the sample name (e.g., NA00001) may be the only attribute present in the original VCF file. Additional attributes may be added to support linkages to the sequencing data, e.g., the datasetGroup and dataset containing the sequencing data corresponding to this sample. Additional dimensional attributes may be added to support fast access to certain quantities, such as counts or average quantities corresponding to a particular variant. A description of the INFO attributes in the comments may be stored as part of the AttributeMetadata.

2-D table Attributes. These attributes are described in the FORMAT fields such as GT, GQ, DP, etc., each of which is a 2-dimensional array. The types of these attributes are also described in the comments. In cases where most variants are not expressed, the default value for the GT attribute may be set, for example, to 0/0. The description of the attributes in the comments may be stored as part of the AttributeMetadata.

Compressors. The compressors for the attributes may be chosen based on the type and characteristics of the attribute. For example, CHROM may be compressed using an enumeration-based scheme followed by gzip, POS may be compressed using delta coding followed by gzip, etc. The sample names (NA00001 etc.) may be efficiently compressed, for example, with a tokenization-based string compressor. Some of the INFO fields may be present for only a small number of variants, and thus may be encoded with a sparse representation. Similarly, the genotypes (GT) may be encoded with a sparse representation or with a specialized compressor for genotypes (e.g. GTC).

The length of certain variable-length attributes may depend on one or more other attributes, e.g., the AF (allele frequency) attribute length may be equal to the number of alternate alleles. In such cases, nDependencies for the compressor may be set to 1 and this dependency may be exploited to boost the compression. Similarly, the value of the GT field can be used as a side information for the compression of the other FORMAT fields, exploiting the dependencies between them.

Chunking and Indexing. The chunking for the main 2d array may be performed depending on the access patterns. If most accesses are for variants in a particular region, then each chunk may include all samples and a small number of variants (e.g., horizontal chunks). If most accesses are for all variants for a particular sample, the chunk may include all variants and a small number of samples (e.g., vertical chunks). If both types of queries are quite common, then it may be better in some cases to use rectangular chunks including a small number of variants and samples. By increasing the size of the chunks, random access performance may be traded off against compression ratio.

For random access based on genomic region, an additional index may be used as indicated in Table 2 (e.g., based on CSI indexing).

TABLE 2

| AttributeIDsIndexed | CHROM, POS |
|---|---|
| IndexType | CSI |
| IndexSize | Size of index |
| IndexData | CSI index structure |

Rather, than specifying the actual file position as done in CSI, the list of chunkIDs may be returned (or indicated) that overlap with the genomic region in question. The positions of these chunks in the file may then be determined from the default index structure. If indel or structural variants are prevalent, CSI indexing may be performed based on both START and END position of the variant. More attributes may be indexed to allow fast random-access queries. For example, the FILTER attribute may be indexed to allow for faster filtering of variants based on whether FILTER=PASS or not.

Protection. The access control policy may take various forms depending, for example, on the use case. For example, certain users might have access to all the data, while others might have access only to variants within certain genomic regions (e.g., as specified by CHROM and POS). Similarly, access may be restricted to only certain samples. In one case, this may require the chunks to be chosen accordingly. Access control may also be imposed at the attribute level, e.g., allowing access to the INFO fields but not the individual sample data.

Metadata. The comment lines (e.g., first three lines) may be retained as part of the FileMetadata. If this is stored as part of an MPEG-G file with sequencing data, the metadata may also include the corresponding dataset groups that contain the sequencing data corresponding to this annotation data.

Tables. In order to allow the data to be displayed at different scales and resolutions, multiple tables may be generated by the system processor with precomputed values for different resolutions. For example, the TableInfo field may store the parameters and other information indicative of the resolution in a predefined format. This may allow a user to query the list of available resolutions without having to read the whole file. Also, the ByteOffset variable for each table may allow direct access to the desired resolution. One or more of the multiple tables may have, for example, a single dimension.

Attributes. In one embodiment, each column may serve as an attribute: chrom (string), chromStart (integer), chromEnd (integer), name (string), score (integer), strand (character), thickStart (integer), thickEnd (integer), itemRGB (8-bit integer array of length 3).

Compressors. The compressors for the attributes may be chosen based on the type and characteristics of the attribute. For example, chrom may be compressed using an enumeration-based scheme followed by gzip or run-length coding, chromStart and chromEnd may be compressed using delta coding followed by gzip, etc. In cases where the values of thickStart and thickEnd are close to chromStart and chromEnd, compression may be improved, for example, by using these values as side information.

In this example, the value of chromStart matches the value of chromEnd on the previous row. One way to exploit this would be to consider chromStart, chromEnd as a single attribute of type "integer array of length 2." This may be done, for example, if the visualization tools understand this alternate representation.

Chunking and Indexing. For random access based on the genomic region, an additional index may be used as shown in Table 4 (based on CSI indexing). Rather than specifying the actual file position as done in CSI, the list of chunkIDs may be indicated that overlap with the genomic region in question. The positions of these chunks in the file may then be determined from the default index structure.

Genome Functional Annotation Data (BED)

TABLE 3

A Simple BED File Example (from UCSC Genome Browser FAQ)

```
browser position chr7:127471196-127495720
browser hide all
track name="ItemRGBDemo" description="Item RGB demonstration" visibility=2
itemRgb="On"
chr7   127471196   127472363   Pos1   0   +   127471196   127472363   255,0,0
chr7   127472363   127473530   Pos2   0   +   127472363   127473530   255,0,0
chr7   127473530   127474697   Pos3   0   +   127473530   127474697   255,0,0
chr7   127474697   127475864   Pos4   0   +   127474697   127475864   255,0,0
chr7   127475864   127477031   Neg1   0   -   127475864   127477031   0,0,255
chr7   127477031   127478198   Neg2   0   -   127477031   127478198   0,0,255
chr7   127478198   127479365   Neg3   0   -   127478198   127479365   0,0,255
chr7   127479365   127480532   Pos5   0   +   127479365   127480532   255,0,0
chr7   127480532   127481699   Neg4   0   -   127480532   127481699   0,0,255
```

Table 3 above shows a section of a BED file, with some annotation data. The system processor may process the information in this file to conform to the unified, standardized file while preserving the data and providing additional functionalities, as described below.

TABLE 4

| AttributeIDsIndexed | chrom, chromStart, chromEnd |
|---|---|
| IndexType | CSI |

TABLE 4-continued

| IndexSize | Size of index |
|---|---|
| IndexData | The CSI index structure |

Rather than specifying the actual file position as done in CSI, the list of chunkIDs may be indicated that overlap with the genomic region in question. The positions of these chunks in the file may then be determined from the default index structure.

Protection. Additionally, the access control policy may take various forms depending on the use case. For example, certain users may have access to all the data, while others may have access only to coarse resolution data (e.g., recall that different resolutions may be stored in different tables). Similarly, access may be restricted to only certain genomic regions. In this case, the chunks may be chosen accordingly.

Single Cell RNAseq Expression Data

Single cell RNAseq expression data may include a sparse two-dimensional matrix of integer/float expression values, where each row corresponds to a gene and each column corresponds to a barcode representing a cell. In this case, the expression values may be stored as a two-dimensional sparse attribute array, while the information associated with the genes becomes the dimension-specific row attributes and the information associated with the barcodes becomes the dimension-specific column attributes. The sparse array may be split into the coordinate stream and the value stream, which are compressed separately, with the row coordinates and the column coordinates for each row being delta coded prior to compression. To allow fast random access, the data may be chunked into a fixed number of genes (rows) per chunk. Finally, an additional B-tree index may be used for selective queries based on gene id, where the index maps the gene id to the chunk containing the gene id and the position of the gene id within the chunk.

This approach was applied to a dataset consisting of 10k brain cells from an E18 mouse, with roughly 31,000 genes, 6,800,000 barcodes and 40 million integer entries in the sparse expression array. The proposed approach using BSC as the final compression layer, reduces the size from 750 MB (uncompressed) to 67 MB, which is more than 2 times smaller than the compressed size when gzip or BSC are applied directly to the original file without any splitting of the columns into attributes or delta coding of the coordinates.

The methods, processes, and/or operations described herein may be performed by code or instructions to be executed by a computer, processor, controller, or other signal processing device. The code or instructions may be stored in a non-transitory computer-readable medium in accordance with one or more embodiments. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods herein.

The processors, compressors, decompressors, managers, selectors, parsers, and other information generating, processing, and calculating features of the embodiments disclosed herein may be implemented in logic which, for example, may include hardware, software, or both. When implemented at least partially in hardware, the processors, compressors, decompressors, managers, selectors, parsers, and other information generating, processing, and calculating features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the processors, compressors, decompressors, managers, selectors, parsers, and other information generating, processing, and calculating features may include, for example, a memory or other storage device for storing code or instructions to be executed, for example, by a computer, processor, microprocessor, controller, or other signal processing device. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods herein.

It should be apparent from the foregoing description that various example embodiments of the invention may be implemented in hardware or firmware. Furthermore, various exemplary embodiments may be implemented as instructions stored on a machine-readable storage medium, which may be read and executed by at least one processor to perform the operations described in detail herein. A machine-readable storage medium may include any mechanism for storing information in a form readable by a machine, such as a personal or laptop computer, a server, or other computing device. Thus, a machine-readable storage medium may include read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Although the various exemplary embodiments have been described in detail with particular reference to certain exemplary aspects thereof, it should be understood that the invention is capable of other embodiments and its details are capable of modifications in various obvious respects. One or more embodiments may be combined with one or more other embodiments to form new embodiments. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

In accordance with one or more embodiments, a system and method for controlling the selective compression and decompression of genomic annotation data includes processing information in one of a plurality of incompatible file formats into a unified file that controls the selective compression and decompression. The annotation data is processed and information is extracted and further processed to support functionalities such as fast query, random access, multiple resolutions (zooms), selective encryption, authentication, access control and traceability. The processing may also be performed to allow for significant compression gains by separating different attributes of the data and allowing the use of specialized compressors for these. Additional processing may also be performed to support metadata and linkages to the sequencing data associated with the annotations, as well as linkages to other annotation data from the same study, allowing seamless integration with the existing MPEG-G file format for sequencing data.

In one or more embodiments, additional processing may be performed to generate protection (access control) information at multiple levels in a hierarchy that allows for fine-grained security settings. Similarly, the metadata and attributes allow an effective way to link different types of annotation data as well as sequencing datasets. The file generated by the processing may be used as a standalone file or as part of an MPEG-G file. Additionally, the generation of such a file, especially for genomic annotation data, provides sufficient flexibility to achieve state-of-the-art compression performance on a variety of data types by incorporating the appropriate compression techniques for the attributes in question.

What is claimed is:

1. A method for compression of data, comprising:
accessing tabulated data in at least two of a plurality of first file formats wherein the at least two of a plurality of first file formats are incompatible with one another;
extracting attributes from the tabulated data;
dividing the tabulated data into chunks;
processing the extracted attributes and chunks into correlated information;
selecting different compressors and dependency attributes for the attributes and chunks identified in the correlated information;
storing global data for compressors shared across chunks;
generating a file in a second file format that includes the correlated information, and further includes information indicative of the different compressors being used to compress the chunks and attributes, wherein the second file format is different from the first file formats; and
generating access control policy information for the correlated information, and integrating the access control policy information into the file of the second file format, wherein the access control policy information includes first information indicating a first level of access for a first portion of the correlated information and second information indicating a second level of access for a second portion of the correlated information, wherein the second level of access is different from a first level of access.

2. The method of claim 1, wherein the correlated information includes at least one table including:
first information indicative of one or more of the attributes, and second information corresponding to chunks associated with the one or more attributes indicated in the first information.

3. The method of claim 2, wherein the first information includes a two-dimensional array of cells and wherein each cell identifies one or more corresponding attributes included in the chunks corresponding to the two-dimensional array of cells.

4. The method of claim 3, wherein the first information includes at least one one-dimensional table of dimension-specific attributes relating to the chunks.

5. The method of claim 1, wherein code of or an executable of at least one of the different compressors is embedded in the file.

6. The method of claim 1, wherein at least one of the different compressors encodes one or more attributes of the tabulated data as a sparse array.

7. The method of claim 1, wherein the tabulated data is divided into chunks of different sizes.

8. The method of claim 1, further comprising:
generating one or more attribute-specific indexes; and
incorporating the one or more attribute-specific indexes into the file of the second format, wherein the attribute-specific indexes enable identification of chunks containing a value or range of a specific attribute of the tabulated data.

9. The method of claim 1, further comprising:
integrating the file in the second file format into an MPEG-G file.

10. The method of claim 1, wherein code of or an executable of at least one of the different compressors is embedded in the file.

11. The method of claim 1, wherein at least one of the different compressors encodes one or more attributes of the tabulated data as a sparse array.

12. An apparatus for compression of data, comprising:
a memory configured to store instructions; and
at least one processor configured to execute the instructions to perform operations including:
accessing tabulated data in at least two of a plurality of first file formats, wherein the at least two of a plurality of first file formats are incompatible with one another;
extracting attributes from the tabulated data;
dividing the tabulated data into chunks;
processing the extracted attributes and chunks into correlated information;
selecting different compressors and dependency attributes for the attributes and chunks identified in the correlated information;
storing global data for compressors shared across chunks; and
generating a file in a second file format that includes the correlated information and further including information indicative of the different compressors used for compressing the chunks and attributes, wherein the second file format is different from the first file formats; and
generating access control policy information for the correlated information, and integrate the access control policy information into the file of the second file format, wherein the access control policy information includes first information indicating a first level of access for a first portion of the correlated information and second information indicating a second level of access for a second portion of the correlated information, and wherein the second level of access is different from a first level of access.

13. The apparatus of claim 12, wherein the correlated information includes at least one table including:
first information indicative of one or more of the attributes, and second information corresponding to chunks associated with the one or more attributes indicated in the first information.

14. The apparatus of claim 13, wherein the first information includes a two-dimensional array of cells and wherein each cell identifies one or more corresponding attributes included in the chunks corresponding to the two-dimensional array of cells.

15. The apparatus of claim 14, wherein the first information includes at least one one-dimensional table of dimension-specific attributes relating to the chunks.

16. The apparatus of claim 12, wherein the tabulated data is divided into chunks of different sizes.

17. The apparatus of claim 12, wherein the at least one processor is configured to execute the instructions to:
   generate one or more attribute-specific indexes; and
   incorporate the one or more attribute-specific indexes into the file of the second format, wherein the attribute-specific indexes enable identification of chunks containing a value or range of a specific attribute of the tabulated data.

18. The apparatus of claim 12, wherein the at least one processor is configured to execute the instructions to integrate the file in the second file format into an MPEG-G file.

* * * * *